United States Patent [19]

Carson et al.

[11] Patent Number: 4,672,066

[45] Date of Patent: Jun. 9, 1987

[54] DERIVATIVES OF 4-ACETYL-3-HYDROXY-2-ALKYL-PHENOXYCARBOXYLIC ACIDS

[75] Inventors: Matthew Carson, Nutley; Ru-Jen L. Han, Princeton Junction; Ronald A. LeMahieu, North Caldwell, all of N.J.

[73] Assignee: Hoffmann-La Roche Inc., Nutley, N.J.

[21] Appl. No.: 725,602

[22] Filed: Apr. 22, 1985

[51] Int. Cl.⁴ ............... C07D 239/26; C07D 213/55; C07D 207/327; A61K 31/44
[52] U.S. Cl. ................................. 514/256; 514/277; 514/346; 514/357; 514/399; 544/335; 546/291; 546/340; 546/342; 548/341
[58] Field of Search ............ 544/335; 546/332, 340, 546/337, 291, 342; 548/341; 514/256, 357, 346, 277, 399

[56] References Cited

FOREIGN PATENT DOCUMENTS 0108592 5/1984 European Pat. Off. .

Primary Examiner—Henry R. Jiles
Assistant Examiner—Dale A. Bjorkman
Attorney, Agent, or Firm—Jon S. Saxe; Bernard S. Leon; William G. Isgro

[57] ABSTRACT

The invention relates to compounds of the formula

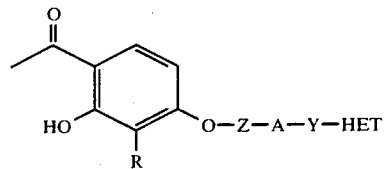

wherein R is hydrogen or lower alkyl, Y is alkylene; Z is alkylene,

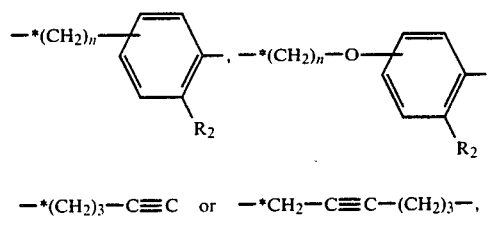

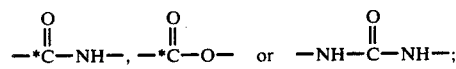

the asterisk herein denotes bonding to the substituted acetophenone; $R_2$ is hydrogen or lower alkoxy; and n is an integer of 1 to 3; A is $$-\overset{*}{C}(=O)-NH-, \quad -\overset{*}{C}(=O)-O- \quad \text{or} \quad -NH-C(=O)-NH-;$$

and HET is a 5-or 6- membered nitrogen containing heterocyclic group, and their acid addition salts. The compounds of formula I of the invention are useful for the treatment of allergic conditions, such as, asthma and cardiovascular diseases, such as, angina and arrhythmias.

43 Claims, No Drawings

DERIVATIVES OF 4-ACETYL-3-HYDROXY-2-ALKYL-PHENOXYCARBOXYLIC ACIDS

BRIEF SUMMARY OF THE INVENTION

The invention relates to phenoxycarboxylic acid derivatives of the formula

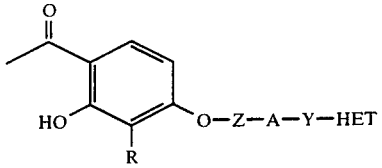

wherein R is hydrogen or lower alkyl; Y is alkylene; Z is alkylene,

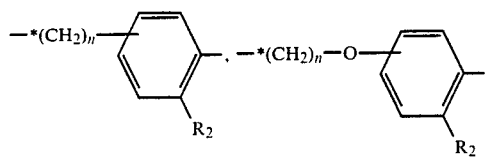

—*(CH$_2$)$_3$—C≡C  or  —*CH$_2$—C≡C—(CH$_2$)$_3$—, the asterisk herein denotes bonding to the substituted acetophenone; R$_2$ is hydrogen or lower alkoxy; n is an integer of 1 to 3; A is

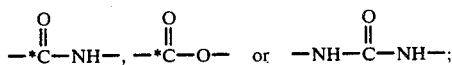

and HET is a 5- or 6- membered nitrogen containing heterocyclic group, and their acid addition salts. The compounds of formula I of the invention are useful for the treatment of allergic conditions, such as, asthma and cardiovascular diseases, such as, angina and arrhythmias.

DETAILED DESCRIPTION OF THE INVENTION

As used herein, the term "lower alkyl" denotes a straight or branched chain aliphatic hydrocarbon of 1 to 7 carbon atoms, for example, methyl, ethyl, propyl, isopropyl, butyl, isobutyl, pentyl, hexyl, pentyl, and the like; preferred is propyl. The term "alkylene" denotes a bivalent straight or branched chain aliphatic hydrocarbon of 1 to 6 carbon atoms, for example, methylene, ethylene, propylene, butylene, 2-methylpropylene, pentylene, hexylene and the like; preferred are propylene, butylene and pentylene. The term "HET" denotes a 5- or 6- membered, nitrogen containing heterocyclic group, for example, 3- or 4- pyridinyl, 3-pyridinyloxy, 3-pyridinylthio, 5- pyrimidinyl, 1H-imidazol-1-yl and the like.

The compounds of the invention are characterized by formula I

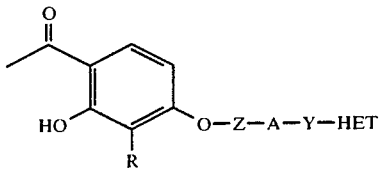

wherein R is hydrogen or lower alkyl; Y is alkylene; Z is alkylene,

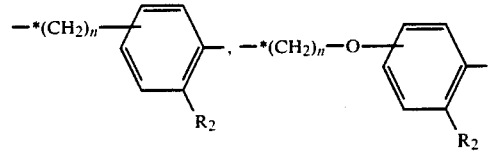

—*(CH$_2$)$_3$—C≡C—  or  —*CH$_2$—C≡C—(CH$_2$)$_3$—, the asterisk denotes bonding to the substituted acetophenone; R$_2$ is hydrogen or lower alkoxy n is an integer of 1 to 3 moiety; A is

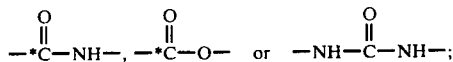

and HET is a 5- or 6- membered nitrogen containing heterocyclic group, and their acid addition salts can be prepared as hereinafter described.

The compounds of formula I wherein R is propyl, Z is

*—CH$_2$C≡C(CH$_2$)$_3$—,

*—(CH$_2$)$_3$C≡C—,  or  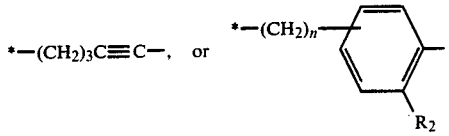

and Y are alkylene are preferred.

Most preferred compounds of the invention are:
5-(4-acetyl-3-hydroxy-2-propylphenoxy-N-[4-(3-pyridinyl)butyl]pentanamide;
6-(4-acetyl-3-hydroxy-2-propylphenoxy)-N-[4-(3-pyridinyl)butyl]hexanamide;
4-(4-acetyl-3-hydroxy-2-propylphenoxy)-N-[4-(3-pyridinyl)butyl]butanamide;
6-(4-acetyl-3-hydroxy-2-propylphenoxy)-N-4-(5-pyrimidinyl)butylhexanamide;
7-(4-acetyl-3-hydroxy-2-propylphenoxy)-N-[4-(3-pyridinyl)butyl]-5-heptynamide;
6-(4-acetyl-3-hydroxy-2-propylphenoxy)-N-[4-(3-pyridinyl)butyl]-2-hexynamide;
4-(4-acetyl-3-hydroxy-2-propylphenoxy)-3-methyl-N-[4-(3-pyridinyl)butyl]butanamide;
4-(4-acetyl-3-hydroxy-2-propylphenoxy)-N-[1-methyl-4-(3-pyridinyl)butyl]butanamide;
N-[5-(4-acetyl-3-hydroxy-2-propylphenoxy)pentyl]-N'-[4-(3-pyridinyl)butyl]urea;
N-[3-(4-acetyl-3-hydroxy-2-propylphenoxy)propyl]-N'-[4-(3-pyridinyl)butyl]urea;
3-[(4-acetyl-3-hydroxy-2-propylphenoxy)methyl]-N-[4-(3-pyridinyl)butyl]benzamide;

4-[(4-acetyl-3-hydroxy-2-propylphenoxy)methyl]-N-[4-3-pyridinyl)butyl]benzamide;
3-[(4-acetyl-3-hydroxy-2-propylphenoxy)methyl]-N-[1-methyl-4-(3-pyridinyl)butyl]benzamide;
4-[(4-acetyl-3-hydroxy-2-propylphenoxy)methyl]-N-[1-methyl-4-(3-pyridinyl)butyl]benzamide;
4-[(4-acetyl-3-hydroxy-2-propylphenoxy)methyl]-2-ethoxy-N-[4-(3-pyridinyl)butyl]benzamide;
3-[(4-acetyl-3-hydroxy-2-propylphenoxy)methyl]-2-ethoxy-N-[4-3-pyridinyl)butyl]benzamide;
2-[3-(4-acetyl-3-hydroxy-2-propylphenoxy)propoxy]-N-[4-(3-pyridinyl)butyl]benzamide; and
3-[3-(4-acetyl-3-hydroxy-2-propylphenoxy)propoxy]-N-[4-(3-pyridinyl)butyl]benzamide.

Additional exemplary compounds of the invention are:

3-(4-acetyl-3-hydroxy-2-propylphenoxy)-N-[4-(3-pyridinyl)butyl]propanamide;
(4-acetyl-3-hydroxy-2-propylphenoxy)-N-[4-(3-pyridinyl)butyl]acetamide;
6-(4-acetyl-3-hydroxy-2-propylphenoxy)-N-[6-(3-pyridinyl)hexyl]hexanamide;
6-(4-acetyl-3-hydroxy-2-propylphenoxy)-N-[3-(3-pyridinyl)propyl]hexanamide;
6-(4-acetyl-3-hydroxy-2-propylphenoxy)-N-[2-(3-pyridinyl)ethyl]hexanamide;
4-(4-acetyl-3-hydroxy-2-propylphenoxy)-N-[6-(3-pyridinyl)hexyl]butanamide;
4-(4-acetyl-3-hydroxy-2-propylphenoxy)-N-[3-(3-pyridinyl)propyl]butanamide;
4-(4-acetyl-3-hydroxy-2-propylphenoxy)-N-[2-(3-pyridinyl)ethyl]butanamide;
8-(4-acetyl-3-hydroxy-2-propylphenoxy)-N-[4-(3-pyridinyl)butyl]octanamide;
7-(4-acetyl-3-hydroxy-2-propylphenoxy)-N-[4-(3-pyridinyl)butyl]heptanamide;
6-(4-acetyl-3-hydroxy-2-propylphenoxy)-N-[4-(1H-imidazol-1-yl)butyl]hexanamide;
6-(4-acetyl-3-hydroxy-2-propylphenoxy)-N-[4-(2-pyridinyl)butyl]hexanamide;
6-(4-acetyl-3-hydroxy-2-propylphenoxy)-N-[2-(4-pyridinyl)butyl]hexanamide;
6-(4-acetyl-3-hydroxy-2-propylphenoxy)-N-[2-(4-pyridinylthio)ethyl]hexanamide;
4-(4-acetyl-3-hydroxy-2-propylphenoxy)-2,2-dimethyl-N-[4-(3-pyridinyl)butyl]butanamide;
4-(4-acetyl-3-hydroxy-2-propylphenoxy)-2-methyl-N-[4-(3-pyridinyl)butyl]butanamide;
4-(4-acetyl-3-hydroxy-2-propylphenoxy)-3-methyl-N-[1-methyl-4-(3-pyridinyl)-butyl]butanamide;
6-(4-acetyl-3-hydroxy-2-propylphenoxy)-N-[1-methyl-4-(3-pyridinyl)butyl]-hexanamide;
N'-[3-[(4-acetyl-3-hydroxy-2-propylphenoxy)methyl]-phenyl]-N-[4-(3-pyridinyl)-butyl]urea;
2-[(4-acetyl-3-hydroxy-2-propylphenoxy)methyl]-N-[4-(3-pyridinyl)butyl]-benzamide;
4-[2-(4-acetyl-3-hydroxy-2-propylphenoxy)ethoxy]-N-[4-(3-pyridinyl)butyl]-benzamide;
3-[2-(4-acetyl-3-hydroxy-2-propylphenoxy)ethoxy]-N-[4-(3-pyridinyl)butyl]-benzamide;
2-[2-(4-acetyl-3-hydroxy-2-propylphenoxy)ethoxy]-N-[4-(3-pyridinyl)butyl]-benzamide;
4-[3-(4-acetyl-3-hydroxy-2-propylphenoxy)propoxy]-N-[4-(3-pyridinyl)butyl]-benzamide;
4-[(4-acetyl-3-hydroxy-2-propylphenoxy)methyl]-2-butoxy-N-[4-(3-pyridinyl)-butyl]benzamide;
4-[(4-acetyl-3-hydroxy-2-propylphenoxy)methyl]-2-ethoxy-N-[1-methyl-4-(3-pyridinyl)butyl]benzamide;
3-[(4-acetyl-3-hydroxy-2-propylphenoxy)methyl]-2-ethoxy-N-[1-methyl-4-(3-pyridinyl)butyl]benzamide;
3-[(4-acetyl-3-hydroxy-2-propylphenoxy)methyl]-N-[6-(3-pyridinyl)hexyl]-benzamide;
3-[(4-acetyl-3-hydroxy-2-propylphenoxy)methyl]-N-[4-(1H-imidazol-1-yl)-butyl]benzamide;
4-[(4-acetyl-3-hydroxy-2-propylphenoxy)methyl]-N-[4-(1H-imidazol-1-yl)-butyl]benzamide; and the like.

The compounds of formula I of the invention, wherein A is

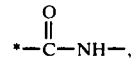

can be prepared as hereinafter described in Reaction Scheme I.

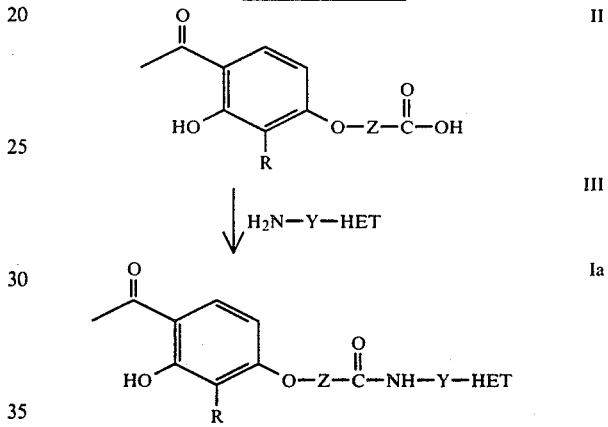

wherein R, Z, Y and HET are previously described.

In Reaction Scheme I, the conversion of an acid of formula II to the desired end product of formula Ia is set forth. More specifically, a compound of formula II is converted to an intermediate acid azide by reaction with diphenylphosphoryl azide in an anhydrous polar solvent, such as, dimethylformamide, at a temperature in the range of from about 0° to about 25° C., preferably at about 5° C., and in the presence of an organic base, such as, a trialkylamine, for example, triethylamine. The reaction mixture containing the acid azide is then treated with an amine of formula III, which are known compounds, at a temperature in the range of from about 0° to about 25° C., to give the corresponding end product of formula Ia, which can be separated by known procedures, for example, crystallization, chromotography and the like.

Alternatively, a compound of formula II is converted to an intermediate imidazolide by treatment with 1,1'-carbonyldiimidazole in an anhydrous inert solvent, such as, tetrahydrofuran, at a temperature in the range of from about 0° to about 25° C., preferably at about 25° C. The obtained imidazolide is immediately allowed to react with an amine of formula III at about 25° to give the corresponding end product of formula Ia.

The compounds of formula I of the invention, wherein A is

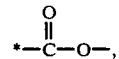

can be prepared as hereinafter described in Reaction Scheme II.

Reaction Scheme II

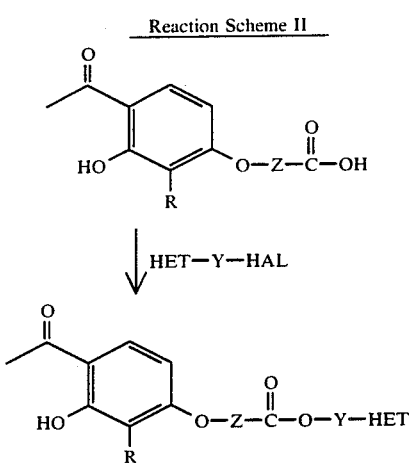

wherein R, Z, Y and HET are as previously described.

In Reaction Scheme II, The conversion of an acid of formula II to the corresponding end product of formula Ib is set forth. A compound of formula II is treated with a compound of formula IV in the presence of an alkali metal carbonate, preferably potassium carbonate, in a solvent, such as, a ketone, for example, acetone, or dimethyl formamide, at a temperature in the range of from about 50° to about 100°, preferably about 70°. An alkali metal iodide, such as, sodium or potassium iodide, is used to accelerate the reaction. The obtained compound of formula Ib can be separated by known procedures, for example, crystallization, chromatography and the like.

The compounds of formula I of the invention, wherein A is

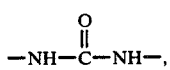

can be prepared as hereinafter described in Reaction Scheme III.

Reaction Scheme III

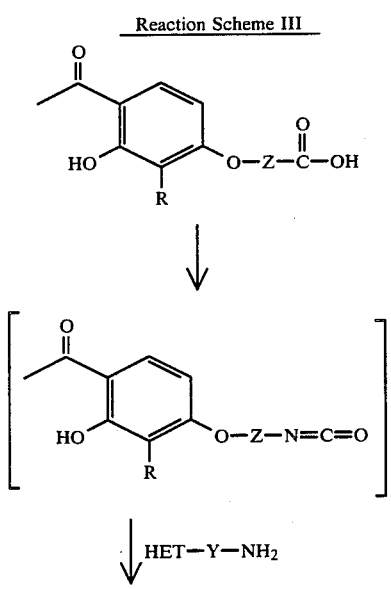

-continued
Reaction Scheme III

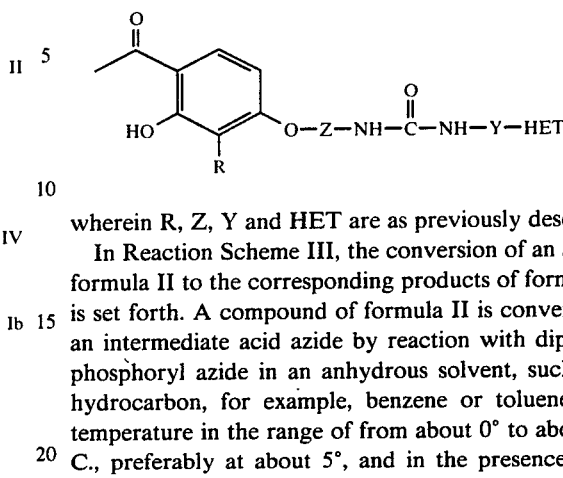

wherein R, Z, Y and HET are as previously described.

In Reaction Scheme III, the conversion of an acid of formula II to the corresponding products of formula Ic is set forth. A compound of formula II is converted to an intermediate acid azide by reaction with diphenylphosphoryl azide in an anhydrous solvent, such as, a hydrocarbon, for example, benzene or toluene, at a temperature in the range of from about 0° to about 25° C., preferably at about 5°, and in the presence of an organic base, such as, a trialkylamine, for example, triethylamine. The acid azide solution is then heated at a temperature in the range of from about 50° to about 100° C. to cause rearrangement to the corresponding isocyanate. After addition of the amine of formula III, heating is continued at a temperature in the range of from about 50° to about 100° to give the corresponding end product of formula Ic. The obtained compound of formula Ic can be separated by known procedures, for example, crystallization, chromatography and the like.

The intermediates of formula II of the invention, wherein Z is alkylene, or

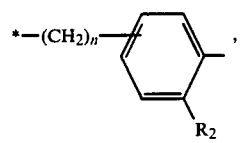

can be prepared as hereinafter described in Reaction Scheme IV.

Reaction Scheme IV

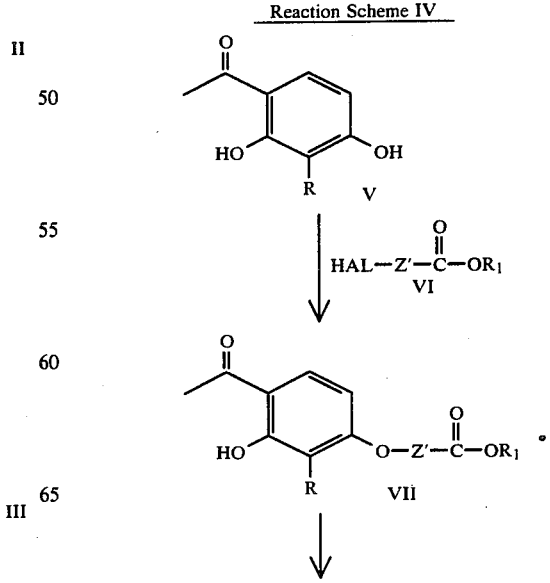

-continued
Reaction Scheme IV

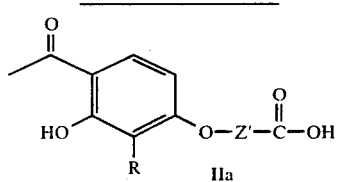

wherein $R_1$ is lower alkyl, $Z'$ is alkylene or

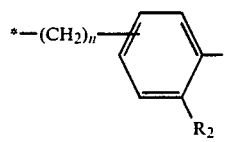

and R, n and HAL are as previously described.

In Reaction Scheme IV, a process for preparing the starting materials of formula IIa is set forth. The reaction between a compound of formula V and a compound of formula VI, which are known compounds or can be prepared according to known procedures, is carried out in an inert solvent, for example, a ketone, preferably acetone or methyl ethyl ketone, or dimethyl formamide in the presence of a base, such as, an alkali metal carbonate, preferably potassium carbonate. The reaction is carried out at a temperature in the range of from about 25° to about 100°. The product of formula VII is converted to the corresponding acid of formula IIa by hydrolysis with an alkali metal hydroxide, such as, sodium hydroxide, in an aqueous alkanol, such as, methanol or ethanol, at a temperature in the range of from about 25° to about the boiling point of the reaction mixture. The obtained compound of formula IIa can be separated by known procedures, for example, by crystallization, chromatography and the like.

The intermediates of formula II of the invention, wherein Z is alkylene, or

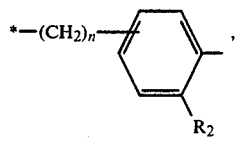

can also be prepared as hereinafter described in Reaction Scheme V.

Reaction Scheme V

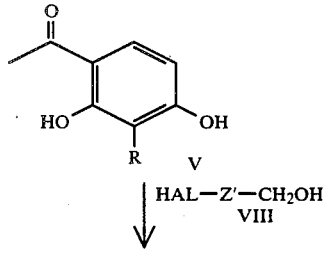

-continued
Reaction Scheme V

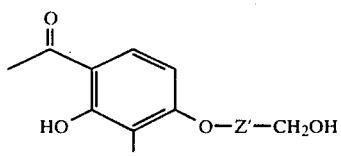

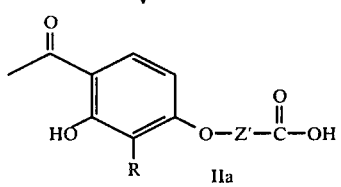

wherein R, $Z'$ and HAL are as previously described.

In Reaction Scheme V, another process for preparing the starting acids of formula IIa is set forth. A compound of formula V, which are known compounds or can be prepared according to known procedures, is alkylated with a halo alcohol of formula VIII, which are known compounds or can be prepared according to known procedures, in a solvent, such as, acetone or dimethyl formamide in the presence of a base, such as, an alkali metal carbonate, preferably, potassium carbonate, at a temperature in the range of from about 50° to about 100° C. An alkali metal iodide may be used to facilitate the reaction. The product obtained of formula IX is then oxidized under standard Jones oxidation conditions, which comprise treatment with chromium trioxide and sulfuric acid in an inert solvent, such as, acetone at a temperature of from about 0° to about 25° C., to yield the corresponding acid of formula IIa. The obtained compound of formula IIa can be separated by known procedures, for example, crystallization, chromatography and the like.

The intermediates of formula II of the invention, wherein Z is alkylene or

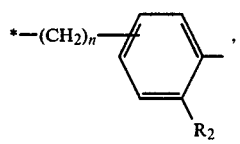

can also be prepared as hereinafter described in Reaction Scheme VI.

Reaction Scheme VI

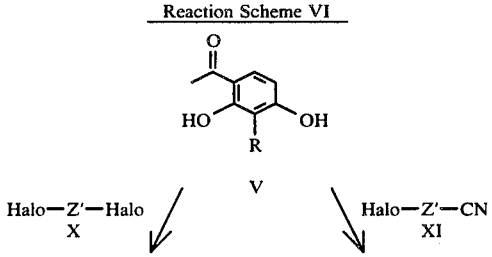

-continued
Reaction Scheme VI

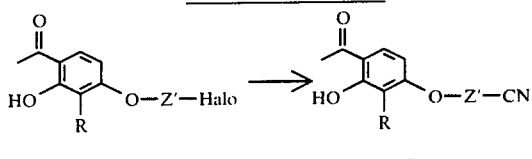

XII  XIII

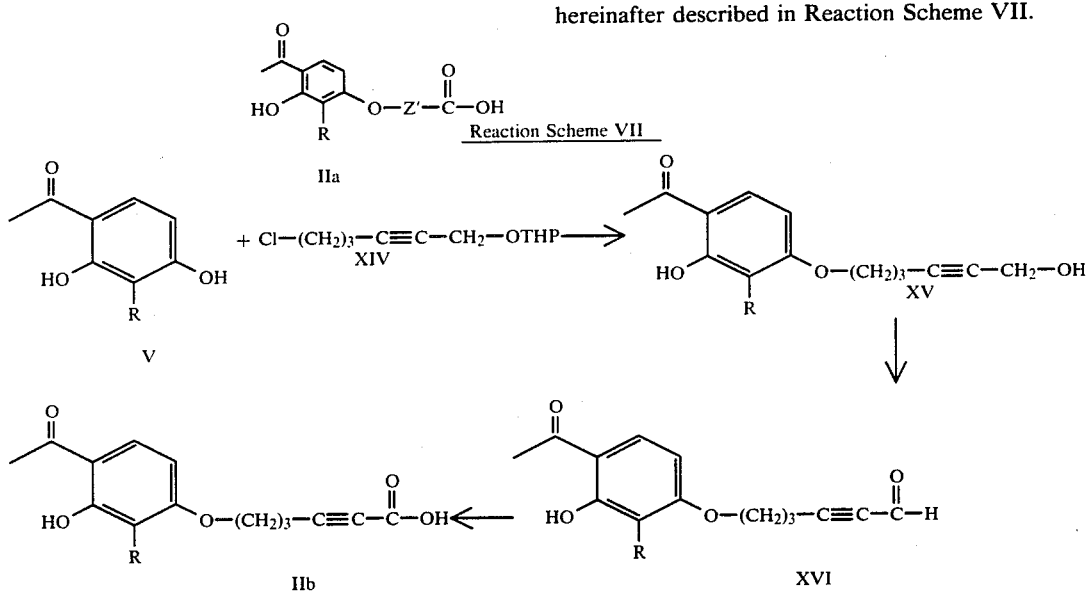

wherein Z' is alkylene and R is as previously described.

In Reaction Scheme VI, another process for preparing the starting acids of formula IIa is set forth. A compound of formula V, which are known compounds or can be prepared according to known procedures, is allowed to react with an excess of a dihalo compound of formula X, which are known compounds, or can be prepared according to known procedures in the presence of an alkali metal carbonate, preferably potassium carbonate, in a solvent, such as, acetone, methyl ethyl ketone or dimethyl formamide. The reaction is carried out at a temperature in the range of from about 50° to about 100° C. The obtained halo compound XII is then allowed to react with an alkali metal cyanide, such as, sodium cyanide in a solvent, such as, dimethyl formamide at a temperature in the range of from about 50° to about 100° C. to give the corresponding nitrile of formula XIII. Alternatively, a nitrile of formula XIII can be prepared directly from a compound of formula V. A compound of formula V is allowed to react with a halo nitrile of formula XI, which are known compounds or can be prepared according to known procedures, in a solvent, such as, acetone or dimethyl formamide in the presence of a base, such as, potassium carbonate at a temperature in the range of from about 50° to about 100° C. A nitrile of formula XIII may be converted to the corresponding starting acid IIa by the following sequence of steps. Treatment of XIII with hydrogen chloride in methanol at a temperature in the range of from 0° to about 25° C. followed by water provides a methyl ester which is hydrolyzed with alkali metal hydroxide in an alcohol solvent. A compound of formula IIa can be separated by known procedures, for example, crystallization, chromotography and the like.

The intermediates of formula II of the invention, wherein Y is —(CH$_2$)$_3$—C≡C—, can be prepared as hereinafter described in Reaction Scheme VII.

wherein R is as previously described.

In Reaction Scheme VII, the reaction between a compound of formula V and XIV, which are known compound or can be prepared according to known procedures, is carried out in an inert solvent, for example, a ketone, preferably acetone or methyl ethyl ketone, or dimethyl formamide, in the presence of a base such as an alkali metal carbonate, preferably potassium carbonate. The reaction is carried out at temperature in the range of from about 25° to about 100° C. Subsequently, the tetrahydropyranyl group is removed by acid hydrolysis. The oxidation of a compound of formual XV to the corresponding compound of formula XVI is carried out by stirring with activated manganese dioxide in an inert chlorinated hydrocarbon solvent, such as, methylene chloride or chloroform, at a temperature in the range of from about 0° to about 30° C.

The oxidation of a compound of formula XVI to the corresponding compound of formula IIb is carried out by treatment of the compound of formula XVI with Jones reagent, that is, chromium trioxide in ION sulfuric acid, using a solvent, such as, a ketone, for example, acetone or methyl ethyl ketone, at a temperature in the range of from about 0° to about 30° C. A compound of formula IIb can be recovered by known procedures, for example, crystallization, chromatography and the like.

The intermediates of formula II of the invention, wherein Y is —CH$_2$—C≡C—(CH$_2$)$_3$—, can be prepared as hereinafter described in Reaction Scheme VIII.

REACTION SCHEME VIII

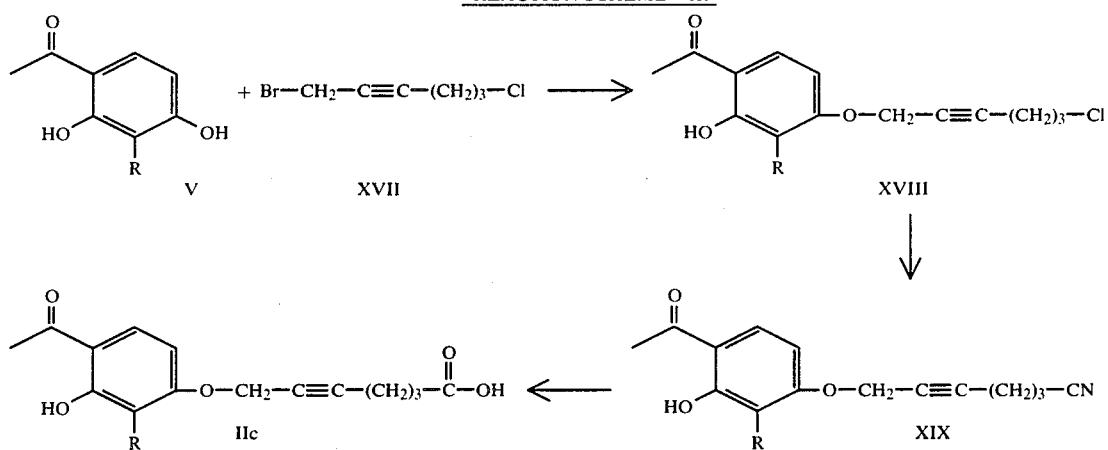

wherein R is as previously described.

In Reaction Scheme VIII, the reaction between a compound of formula V and XVII, which are known compounds or can be prepared according to known procedures, is carried out in an inert solvent, for example, a ketone, preferably acetone or methyl ethyl ketone, or dimethyl formamide in the presence of a base, such as, an alkali metal carbonate, preferably potassium carbonate. The reaction is carried out a temperature in the range of from about 25° to about 100° C.

The corresponding compound of formula XVIII that is obtained is then allowed to react with an alkali metal cyanide, such as, sodium cyanide in the presence of sodium iodide in a solvent, such as, dimethylformamide, at a temperature in the range of from about 50° to about 100° C. to give the corresponding compound of formula XIX.

The nitrile of formula XIX is hydrolyzed to the corresponding compound of formula IIc by treatment with an alkali metal hydroxide, such as, sodium hydroxide, in a solvent, such as, ethylene glycol or propylene glycol, at an elevated temperature in the range of from about 80° to about 150°. A compound of formula IIc can be recovered by known procedures, for example, crystallization, chromatography and the like.

REACTION SCHEME IX

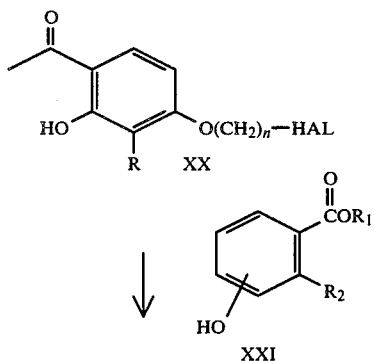

-continued
REACTION SCHEME IX

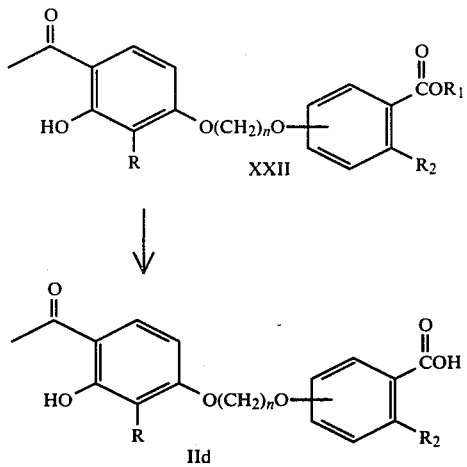

wherein R, $R_1$, $R_2$, n and HAL are as previously described.

In Reaction Scheme IX, a process for preparing the intermediates of formula IId is set forth. The reaction between a compound of formula XX and a compound of formula XXI, which are known compounds or can be prepared according to known procedures, is carried out in an inert solvent, for example, a ketone, preferably acetone or methyl ethyl ketone, or dimethyl formamide in the presence of a base, such as, an alkali metal carbonate, preferably potassium carbonate. The reaction is carried out at a temperature in the range of from about 25° to about 100°. The product ester of formula XXII is converted to the corresponding acid of formula IId by hydrolysis with an alkali metal hydroxide such as sodium hydroxide in an aqueous alcohol such as methanol or ethanol at a temperature in the range of from about 25° to about the boiling point of the reaction mixture. The obtained acid of formula IId can be separated by known procedures, for example, by crystallization and the like.

The compounds of formula I above are basic compounds which form acid addition salts with inorganic or organic acids. More particularly, the compounds of formula I form, with pharmaceutically acceptable organic or inorganic acids, pharmaceutically acceptable acid addition salts, for example, hydrohalides, such as, hydrochloride, hydrobromide or hydroiodide, other mineral acids salts, such as, sulfate, nitrate, phosphate or the like, alkyl- and mono-aryl sulfonates, such as, ethanesulfonate, toluenesulfonate, benzenesulfonate, or the like, other organic acid salts, such as, acetate, tartrate, maleate, citrate, benzoate, salicylate, ascorbate, or the like. Non-pharmaceutically acceptable acid addition salts of the compounds of formula I above can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable anion.

The compounds of formula I are antagonists of slow reacting substance of anaphylaxis (SRS-A; leukotrienes $C_4$, $D_4$ and $E_4$), antagonists of platelet activating factor (PAF) and inhibitors of thromboxane $A_2$ synthesis. Accordingly, the compounds of formula I, including their salts, are useful for the treatment of certain allergic conditions, such as, asthma, skin afflictions, hay fever, chronic bronchitis, allergic conditions of the eye and allergic condition of the gastrointestinal tract, such as, food allergies. The compounds of formula I are also useful for treatment of various cardiovascular diseases involving platelet aggregation, such as, angina, arrhythmias or the like.

The activity and utility of the compounds of formula I and their salts can be demonstrated in warm blooded animals utilizing the test procedures hereinafter described.

PAF Radioreceptor Binding Assay

Platelet rich plasma is prepared by centrifugation of citrate-treated dog blood. Acidification to pH 6.5 with 0.15 M citric acid and centrifugation for 10 minutes at 1000 xg yields a platelet pellet which is then washed by resuspension in EDTA-Phosphate Buffered Saline (PBS) and recentrifuged. The washed platelet preparation is adjusted to $2 \times 10^7$ platelets/50 $\mu$l in 0.1% BSA-PBS.

To a 400 $\mu$l microfuge tube containing 50 $\mu$l silicone oil (specific gravity 1.023) is added buffer, PAF standard or antagonist, to bring the aqueous volume to 150 $\mu$l. 50 $\mu$l of $^3$H-PAF (10,000 cpm, 45 Ci/mM) is added followed by $2 \times 10^7$ dog platelets. After mixing, incubating for 10 minutes at room temperature, and centrifuging for 1 minute in a Beckman Microfuge B (8000 xg), the pellet is removed by clipping off the tip of the tube, the platelets are solubilized with 200 $\mu$l of 50% methanol, and counted in 10 ml of Aquasol. A curve of 50–2500 pg/tube is obtained within 10 minutes of incubation which demonstrates high specificity and correlation with biological activity for PAF and its analogs. Results obtained with representative compounds of the present invention in this assay are summarized hereinafter in Tables I, II and III.

Thromboxane Synthase Inhibition, In Vitro $TXA_2$ synthase activity is measured by following the conversion of $^{14}$C-prostaglandin endoperoxide ($PGH_2$) to $^{14}$C-thromboxane $A_2$ ($TXA_2$) using microsomal fractions from human platelets as enzyme source. In the aqueous incubation medium, the $TXA_2$ decomposes rapidly into $TXB_2$. The amount of $TXA_2$ synthase is adjusted so that under the conditions of the assay approximately 80-90% of the substrate, $PGH_2$, is converted to product in control tubes. To prepare $^{14}$C-$PGH_2$, $^{14}$C-AA (50-60 mCi/mmole; Rose Chem.) is incubated with sheep seminal vesicular gland microsomes for 1.5 minutes at 37° C. and then the $^{14}$C-$PGH_2$ is extracted with diethylether, purified on columns of Sephadex LH-20 or silicic acid, and stored in acetone at $-70°$ C. Incubations are done as follows. Sufficient $^{14}$C-$PGH_2$ yield a final substrate concentration of 10 $\mu$M ($\sim$30,000 cpm) is added to the incubation tubes and then the acetone is removed under nitrogen. The tubes are placed in an ice bath and then 215 $\mu$l of ice cold phosphate buffered saline, 10 $\mu$l of ethanol (control) or of test drug in ethanol, and 25 $\mu$l of the microsomal suspension are added with mixing in that order as rapidly as possible. The tubes are incubated at 22° C. for 2 minutes, the reaction is stopped and then the radioactive products and the unconverted $PGH_2$ are extracted and analyzed by thin layer chromatography. The amount of $^{14}$C-$PGH_2$ converted to products is used as analyzed by thin layer chromatography. The amount of $^{14}$C-$PGH_2$ converted to products was used as a measure of $TXA_2$ synthase activity. Inhibitors were tested initially at a final concentration of 100 $\mu$M. Results obtained with representative compounds of the present invention in this assay are summarized hereafter in Table I, II and III.

Guinea Pig Ileum, In Vitro

The guinea pig ileum bioassay system has been described by Orange and Austen, Adv. Immunol. 10: 104–144 (1959). A 1.5 cm segment is removed from animals weighting 300–400 g. and suspended in an organ bath containing 10 ml. of Tyrodes solution with $10^{-6}$ M atropine sulfate and $10^{-6}$ M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of 3.5 $\times 10^{-8}$ M. Results obtained with representative compounds of the present invention in this assay are summarized hereafter in Table I, and II.

TABLE I

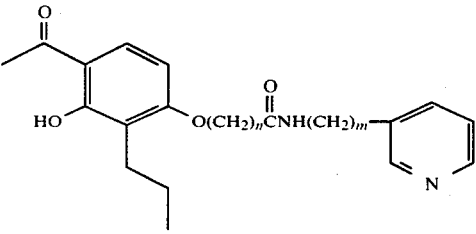

| n | m | PAF Binding IC$_{50}$(μM) | TXA$_2$ Syn. Inhib. % at 0.1 M(1μM) | SRS-A Antagonism IC$_{50}$(μM) |
|---|---|---|---|---|
| 7 | 4 | 1 | 62 | — |
| 6 | 4 | 1 | 64(93) | — |
| 5 | 4 | 0.7 | 52 | 6 |
| 4 | 4 | 1.0 | 78 | — |
| 3 | 4 | 0.25 | 29(89) | 5 |
| 2 | 4 | 1 | 36(77) | — |
| 1 | 4 | 1.5 | 10(81) | — |
| 5 | 6 | 1 | 62(90) | — |
| 5 | 3 | 2.0 | 13(78) | — |
| 5 | 2 | 0.5 | 15(35) | — |
| 3 | 6 | 1 | 41(83) | — |
| 3 | 3 | 1.5 | 9(51) | — |
| 3 | 2 | 0.4 | 10(8) | — |

TABLE II

| R | PAF Binding IC$_{50}$(μM) | TXA$_2$ Synth. Inhib. % at 0.1 M(1μM) | SRS Antagonism IC$_{50}$(μM) |
|---|---|---|---|
| —(CH$_2$)$_5$C(O)NH(CH$_2$)$_4$—N(imidazole) | 1 | 39(87) | |
| —(CH$_2$)$_5$C(O)NH(CH$_2$)$_4$—(2-pyridyl) | 1 | (0) | |
| —(CH$_2$)$_5$C(O)NH(CH$_2$)$_4$—(5-pyrimidinyl) | 0.55 | 24(66) | 10 |
| —(CH$_2$)$_5$C(O)NH(CH$_2$)$_2$S—(3-pyridyl) | 1 | 0(35) | 1 |
| —(CH$_2$)$_5$C(O)NH(CH$_2$)$_4$O—(3-pyridyl) | 1 | 80(93) | |
| —(CH$_2$)$_5$C(O)NH(CH$_2$)$_2$—(4-pyridyl) | 1.75 | (0) | |
| —CH$_2$C≡C(CH$_2$)$_3$C(O)NH(CH$_2$)$_4$—(3-pyridyl) | 0.6 | 63 | 0.7 |

TABLE II-continued

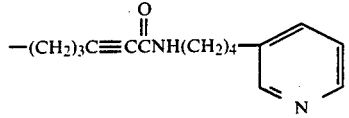

| R | PAF Binding IC$_{50}$(μM) | TXA$_2$ Synth. Inhib. % at 0.1 M(1μM) | SRS Antagonism IC$_{50}$(μM) |
|---|---|---|---|
| —(CH$_2$)$_3$C≡CCNH(CH$_2$)$_4$—(3-pyridyl) | 0.5 | 45(88) | |

TABLE III

![structure with OCH$_2$CH(R)—C(R$_1$)(R$_2$)—CNHCH(R$_3$)(CH$_2$)$_3$-pyridyl]

| R | R$_1$ | R$_2$ | R$_3$ | PAF Binding IC$_{50}$ (μM) | TXA$_2$ Synth. Inhib. % at 0.1 M (1 μM) |
|---|---|---|---|---|---|
| H | H | H | H | 0.25 | 29(89) |
| H | Me | Me | H | 1 | 20(55) |
| Me | H | H | H | 0.2 | 9(77) |
| H | Me | H | H | 1 | 14(70) |
| H | H | H | Me | 0.3 | 26(77) |
| Me | H | H | Me | 1 | 34(78) |

![structure with O(CH$_2$)$_n$NHCNH(CH$_2$)$_m$-pyridyl]

| n | m | PAF Binding IC$_{50}$ (μM) | TXA$_2$ Synth. Inhib. % at 0.1 M (1 μM) |
|---|---|---|---|
| 5 | 4 | 0.9 | 64(89) |
| 3 | 4 | 0.7 | 61(93) |

LTE$_4$-Induced Guinea Pig Bronchoconstriction Test

In this test system, the ability of a drug to inhibit the bronchoconstriction induced in guinea pigs by leukotriene E$_4$(LTE$_4$) is measured. A maximally constrictory dose of LTE$_4$ is injected into guinea pigs which have been pretreated with propranolol (0.1 mg/kg, i.v.) for 5 minutes prior to challenge. The bronchoconstriction (in cm H$_2$O) elicited in animals pretreated intravenously for 30 seconds (at 10 mg/kg) or orally for 2 hours (at 100 mg/kg) with the test drug prior to LTE$_4$ challenge is compared to that elicited in the absence of the test compound to determine the in vivo activity of the drug.

Representative compounds of the invention: 6-(4-acetyl-3-hydroxy-2-propylphenoxy)-N-[4-(3-pyridinyl)-butyl]hexanamide hydrochloride and 6-(4-acetyl-3-hydroxy-2-propylphenoxy)hexanoic acid, 3-(3-pyridinyl)propyl ester hydrochloride gave 95% and 87% inhibition, respectively, when tested at 10 mg/kg i.v.

PAF-Induced Guinea Pig Bronchoconstriction Test

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted in the trachea and connected to a Statham pressure transducer. Propranolol (0.1 mg/kg) is administered intravenously five minutes before challenge with synthetic PAF, the animals's skeletal muscles are then paralyzed with succinylcholine (1.2 mg/kg i.v.), and the animal is respirated using a Harvard small animal respirator operating at 40 breaths/min and 2.5 cc stroke volume. Under these conditions PAF induces a dose-dependent increase in ventilatory pressure over a dose range of 0.5 to 5 pg/kg i.v. The bronchoconstrictive effect of PAF occurs at approximately a 10-fold lower dose than that obtained with LTE. For screening purposes animals are challenged with a single dose of PAF (10 pg/kg i.v.).

Test compounds are screened by either the intravenous route (1.0 mg/kg i.v., 1 min pretreatment) or oral route (100 mg/kg p.o., 2 hour pretreatment). The peak increase in ventilatory pressure (cm H$_2$O) is recorded for three control animals and five drug-treated animals and the percent inhibition determined.

Representative compounds of the invention:
4-(4-acetyl-3-hydroxy-2-propylphenoxy)-N-[4-(3-pyridinyl)butyl]butanamide;
6-(4-acetyl-3-hydroxy-2-propylphenoxy)-N-[4-(3-pyridinyl)butyl]-2-hexynamide;
N-[5-(4-acetyl-3-hydroxy-2-propylphenoxy)pentyl]-N'-[4-(3-pyridinyl)butyl]urea;
4-[(4-acetyl-3-hydroxy-2-propylphenoxy)methyl]-N-[1-methyl-4-(3-pyridinyl)butyl]benzamide;
3-[(4-acetyl-3-hydroxy-2-propylphenoxy)methyl]-2-ethoxy-N-[4-(3-pyridinyl)butyl]benzamide;
4-[(4-acetyl-3-hydroxy-2-propylphenoxy)methyl]-2-ethoxy-N-[4-(3-pyridinyl)butyl]benzamide;

gave 64±12, 98±10, 68±10, 85±8, 96±2 and 96±1% inhibition, respectively, when tested at 1.0 mg/kg i.v.

PAF-Induced Rat Skin Wheal Test

This test evaluates the ability of compounds to inhibit PAF-induced increases in vascular permeability in the skin of Sprague-Dawley rats. PAF induces a dose-dependent skin wheal response in this system over a dose range of 0.0001 to 1 pg/0.05 ml injection. The profound vasoactive activity of PAF is emphasized by the fact that the maximum skin wheal response is considerably greater than that obtained with LTE and an $EC_{50}$ response is elicited at a 10-fold lower dose. For drug screening purposes, 5 ng of PAF is injected intradermally into anesthetized rats which had been pretreated for 30 minutes with an antihistamine (pyrilamine maleate, 50 mg/kg, i.p.) and an antiserotonin compound (methylsergide maleate, 4 mg/kg, i.p.). Immediately thereafter, the test compound is injected intravenously into the tail vein of the animal. This is followed by an intravenous injection of Evan's blue dye (0.5% in saline). Thirty minutes later the animals are sacrificed and the increase in vascular permeability induced by the migration of dye into the injection point in the skin is determined. For this purpose, rats are sacrificed by cervical dislocation, the dorsal skin is removed, the long and short axis of each animal is measured with a metric vernier caliper and the average diameter is obtained.

Representative compounds of the invention, 6-(4-acetyl-3-hydroxy-2-propylphenoxy)-N-[4-(3-pyridinyl)-butyl]-2-hexynamide and 4-[(4-acetyl-3-hydroxy-2-propylphenoxy)methyl]-N-[1-methyl-4-(3-pyridinyl)-butyl]benzamide gave 62±3 and 63±4% inhibition when respectively tested at 5 mg/kg i.v. (1 min. pretreatment).

Leukotriene $D_4$ ($LTD_4$) Induced Arrhythmia Test

Male Hartley guinea pigs are anesthetized with sodium pentobarbital and prepared for monitoring direct blood pressure and injecting drugs intravenously by catheterizing the right carotid artery and right jugular vein. Blood pressure, heart rate, and Lead II ECG are monitored in the conscious animal 24 hours later.

Intravenous administration of $LTD_4$ (2.5 pg/kg) is associated with an increase in blood pressure lasting approximately 1-2 minutes followed by a decrease lasting approximately 5-15 minutes (FIG. 3). Abnormal beats consisting of premature ventricular contractions, ST elevation or depression, atrioventricular conduction block, or dissociated p waves begin during the rise in blood pressure; the peak effect occurs approximately 40 seconds after $LTD_4$. The percent of abnormal beats was quantitated by determining the number present during the first 2 minutes after injection and calculating the percent increase above the control level. During the hypotensive response, the animal usually collapses during the 2nd or 3rd minute after $LTD_4$.

Results with representative compounds of the invention given at 10 mg/kg i.v. 5 min. before the $LTD_4$ are shown in Table IV.

TABLE IV

Inhibition of $LTD_4$ Induced Arrhythmias in Conscious Guinea Pigs (10 mg/kg iv)

| Structure | ↑ XABP (Δmm Hg) | Arrhy's (R/T) | ↓ XABP (Δmm Hg) |
|---|---|---|---|
| Saline Control | 30 ± 4 | 12/12 | 45 ± 4 |
| (4-acetyl-3-hydroxy-2-propylphenoxy)-pentanoyl-N-(4-(3-pyridinyl)butyl), O(CH₂)₅CNH(CH₂)₄-pyridinyl | 6 ± 3 | 0/5 | −16 ± 6 |
| (4-acetyl-3-hydroxy-2-propylphenoxy)-propanoyl analog, O(CH₂)₃CNH(CH₂)₄-pyridinyl | 6 ± 6 | 0/3 | −26 ± 8 |
| pyrimidinyl analog, O(CH₂)₅CNH(CH₂)₄-pyrimidinyl | 32 ± 2 | 1/3 | −44 ± 5 |
| alkyne analog, OCH₂C≡C(CH₂)₃CNH(CH₂)₄-pyridinyl | 18 ± 4 | 1/3 | −44.5 |

The compounds of formula I and their pharmaceutically acceptable salts can be administered orally or parenterally as anti-allergic agents, for example, in the prophylactic treatment of bronchial asthma, with dosage adjustments for individual requirements. They can be administered therapeutically, for example, orally or parenterally, by incorporating a therapeutic dosage in a conventional dosage form, such as tablets, capsules, elixirs, suspensions, solutions or the like. They can be administered in mixture with conventional pharmaceutical carriers or excipients, such as, for example, corn starch, calcium stearate, magnesium carbonate, calcium silicate, dicalcium phosphate, talc, lactose, and the like. Moreover, they can be administered in the presence of buffers, or agents used to adjust to isotonicity and the pharmaceutical dosage forms can, if desired, be subjected to conventional pharmaceutical expedients such as, for example, sterilization. As stated above, the dosage can be adjusted to individual requirements. They can also contain other therapeutically valuable substances.

The frequency with which any such dosage form will be administered to a mammal will vary, depending upon the quantity of active medicament present therein and the needs and requirements of the mammal. Dosages of a compound of formula 1 and its pharmaceutically acceptable salts contemplated for use in practicing the invention are in the range of from about 100 to about 1500 mg per day, either as a single dose or in divided doses. It is to be understood, however, that the above description and dosage strengths and the tablet and capsule descriptions set forth herein are exemplary only and that they do not, to any extent, limit the scope or practice of this invention.

The Examples which follow further illustrate the invention. All temperatures are stated in degrees Centigrade unless otherwise mentioned.

The Examples which follow further illustrate the invention. All temperatures are given in degrees Centigrade. Melting points were determined on a Buchi capillary melting point apparatus and are uncorrected. Spectra (IR, UV, MS, and NMR) were obtained on all compounds and were consistent with the assigned structure.

EXAMPLE 1

Preparation of
5-(4-Acetyl-3-hydroxy-2-propylphenoxy-N-[4-(3-pyridinyl)butyl]pentanamide Procedure A To a solution of 0.686 g 5-(4-acetyl-3-hydroxy-2-propylphenoxy)-pentanoic acid in 10 mL anhydrous dimethylformamide stirred at 5° was added 0.55 mL of diphenylphosphoryl azide dropwise followed by 0.70 mL of triethylamine added dropwise. The reaction mixture was stirred at 5° for 1.5 hours and then 0.385 g of 3-pyridine butanamine was added dropwise. The reaction mixture was stirred at 5° for 3 hours and then at 25° for 16 hours. The solvent was removed in vacuo and the residual oil was dissolved in ethyl acetate and the solution was washed with saturated sodium bicarbonate solution and with saturated sodium chloride solution. The dried (over magnesium sulfate) extract was concentrated in vacuo to an oil which was chromatographed on 40 g silica gel. Elution with methylene chloride (90): 95% methanol (10): conc. ammonium hydroxide (0.05) gave a yellow oil which was crystallized from acetone-hexane. Filtration gave 0.665 g, mp 76°-78°, (67% yield) of 5-(4-acetyl-3-hydroxy-2-propylphenoxy)-N-[4-(3-pyridinyl)butyl]pentanamide the title compound.

Analysis Calculated for $C_{25}H_{34}N_2O_4$: C, 70.40; H, 8.02; N, 6.57. Found: C, 70.50, H, 8.00; N, 6.55.

EXAMPLE 2

Preparation of
8-(4-Acetyl-3-hydroxy-2-propylphenoxy)-N-[4-(3-pyridinyl)butyl]octanamide 8-(4-Acetyl-3-hydroxy-2-propylphenoxy)octanoic acid was allowed to react with 3-pyridine butanamine according to procedure A and the product was purified by high performance liquid chromatography (HPLC) to give 8-(4-acetyl-3-hydroxy-2-propylphenoxy)-N-[4-(3-pyridinyl)butyl]octanamide, the title compound, mp 48°-51° (from ether-hexane) in 83% yield.

Analysis Calculated for $C_{28}H_{40}N_2O_4$: C, 71.76; H, 8.60; N, 5.98. Found: C, 71.60; H, 8.96; N, 5.96.

EXAMPLE 3

Preparation of
7-(4-Acetyl-3-hydroxy-2-propylphenoxy)-N-[4-(3-pyridinyl)butyl]heptanamide 7-(4-Acetyl-3-hydroxy-2-propylphenoxy)heptanoic acid was allowed to react with 3-pyridine butanamine according to procedure A and the product was purified by chromatography on silica gel to give 7(4-acetyl-3-hydroxy-2-propylphenoxy)-N-[4-(3-pyridinyl)butyl]-heptanamide, the title compound, mp 57°-59° (from acetone-hexane) in 75% yield.

Analysis Calculated for $C_{27}H_{38}N_2O_4$: C, 71.34; H, 8.43; N, 6.16. Found: C, 71.31; H, 8.32; N, 6.12.

EXAMPLE 4

Preparation of
6-(4-Acetyl-3-hydroxy-2-propylphenoxy)-N-[4-(3-pyridinyl)butyl]hexanamide hydrochloride 6-(4-Acetyl-3-hydroxy-2-propylphenoxy)hexanoic acid was allowed to react with 3-pyridine butanamine according to procedure A, the product was purified by HPLC and then converted to the hydrochloride to give the 6-(4-acetyl-3-hydroxy-2-propylphenoxy)-N-[4-(3-pyridinyl)butyl]hexanamide hydrochloride, title compound, mp 127-132° (from acetone-hexane) in 85% yield.

Analysis Calculated for $C_{26}H_{36}N_2O_4$ HCl: C, 65,46; H, 7.82; N, 5.87; Cl$^-$, 7.43. Found: C, 65.24; H, 7.74; N, 5.74; Cl$^-$, 7.61.

EXAMPLE 5

Preparation of
4-(4-Acetyl-3-hydroxy-2-propylphenoxy)-N-[4-(3-pyridinyl)butyl]butanamide 4-(4-Acetyl-3-hydroxy-2-propylphenoxy)butanoic acid was allowed to react with 3-pyridine butanamine according to procedure A and the product was purified by HPLC to give 4-(4-acetyl-3-hydroxy-2-propylphenoxy)-N-[4-(3-pyridinyl)butyl]butanamide, the title compound, mp 80°-82° (from ether) in 68% yield.

Analysis Calculated for $C_{24}H_{32}N_2O_4$: C, 69.88; H, 7.82; N, 6.79. Found: C, 69.96; H, 7.98; N, 6.77.

EXAMPLE 6

Preparation of
3-(4-Acetyl-3-hydroxy-2-propylphenoxy)-N-[4-(3-pyridinyl)butyl]propanamide Procedure B To a solution of 0.700 g of 3-(4-acetyl-3-hydroxy-2-propylphenoxy)-propanoic acid and 0.469 g of 1.1'-carbonyldiimidazole in 25 mL of anhydrous tetrahydrofuran at 25° was added 0.434 g of 3-pyridine butanamine. The reaction mixture was stirred for 2 hours and then the solvent was removed in vacuo. The residual oil was dissolved in ethyl acetate and the solution was washed with sodium bicarbonate solution and with saturated sodium chloride solution. The crude product was chromatographed on 40 g of silica gel. Elution with methylene chloride (90): 95% methanol (10): conc. ammonium hydroxide (0.05) gave the pure product which was recyrstallized from methylene chloride-ether to give 3-(4-acetyl-3-hydroxy-2-propylphenoxy)-N-[4-(3- pyridinyl)butyl]propanamide, the title compound, mp 110°–112°, in 63% yield.

Analysis Calculated for $C_{23}H_{30}N_2O_4$: C, 69.32; H, 7.59; N, 7.03. Found: C, 69.08; H, 7.57; H, 7.57; N, 7.07.

EXAMPLE 7

Preparation of
(4-Acetyl-3-hydroxy-2-propylphenoxy)-N-[4-(3-pyridinyl)butyl]acetamide (4-Acetyl-3-hydroxy-2-propylphenoxy)acetic acid was allowed to react with 3-pyridine butanamine according to procedure A and the product was purified by chromatography on silica gel to give (4-acetyl-3-hydroxy-2-propylphenoxy)-N-[4-(3-pyridinyl)butyl]acetamide, the title compound, mp 95°–97° (from methylene chloride-ether) in 57% yield.

Analysis Calculated for $C_{22}H_{28}N_2O_4$: C, 68.73; H, 7.34; N, 7.29. Found: C, 68.41; H, 7.41 ; N, 7.13.

EXAMPLE 8

Preparation of
6-(4-Acetyl-3-hydroxy-2-propylphenoxy)-N-[6-(3-pyridinyl)hexyl]hexanamide 6-(4-Acetyl-3-hydroxy-2-propylphenoxy)hexanoic acid was allowed to react with 3-pyridine hexanamine according to procedure A an the product was purified by HPLC to give 6-(4-acetyl-3-hydroxy-2-propylphenoxy)-N-[6-(3-pyridinyl)-hexly]hexanamide, the title compound, mp 56°–58° (from ether) in 76% yield.

Analysis Calculated for $C_{28}H_{40}N_2O_4$: C, 71.76; H, 8.60; N, 5.98. Found: C, 71.84; H, 8.62; N, 5.96.

EXAMPLE 9

Preparation of
6-(4-Acetyl-3-hydroxy-2-propylphenoxy)-N-[3-(3-pyridinyl)propyl]hexanamide 6-(4-Acetyl-3-hydroxy-2-propylphenoxy)hexanoic acid was allowed to react with 3-pyridine propanamine according to procedure A and the product was purified by chromatography on silica gel to give 6-(4-acetyl-3-hydroxy-2-propylphenoxy)-N-[3-(3-pyridinyl)propyl]-hexanamide the title compound, mp 83°14 85° (from methylene chloride-ether) in 87% yield.

Analysis Calculated for $C_{25}H_{34}N_2O_4$: C, 70.40; H, 8.03; N, 6.57. Found: C, 70.27; H, 8.02; N, 6.52.

EXAMPLE 10

Preparation of
6-(4-Acetyl-3-hydroxy-2-propylphenoxy)-N-[2-(3-pyridinyl)ethyl]hexanamide 6-(4-Acetyl-3-hydroxy-2-propylphenoxy)hexanoic acid was allowed to react with 3-pyridine ethanamine according to procedure A and the product was purified by chromatography on silica gel to give 6-(4-acetyl-3-hydroxy-2-propylpheoxy)-N-[2-(3-pyridinyl)ethyl]hexanamide, the title compound, mp 76°–78° (from acetone-hexane) in 76% yield.

Analysis Calculated for $C_{24}H_{32}N_2O_4$: C, 69.88; H, 7.82; N, 6.79. Found: C, 69.7I; H, 7.77; N, 6.77.

EXAMPLE 11

Preparation of
4-(4-Acetyl-3-hydroxy-2-propylphenoxy)-N-[6-(3-pyridinyl)hexyl]butanamide 4-(4-Acetyl-3-hydroxy-2-propylphenoxy)butanoic acid was allowed to react with 3-pyridine hexanamine according to procedure A and the product was purified by chromatography on silica gel to give 4-(4-acetyl-3-hydroxy- 2-propylphenoxy)-N-[6-(3-pyridinyl)hexyl]-butanamide, the title compound, mp 69°–71° (from ether-hexane) in 84% yield.

Analysis Calculated for $C_{26}H_{36}N_2O_4$: C, 70.88; H, 8.24; N, 6.36. Found: C, 70.87; H, 8.30; N, 6.38.

EXAMPLE 12

Preparation of
4-(4-Acetyl-3-hydroxy-2-propylphenoxy)-N-[3-(3-pyridinyl)propyl]butanamide 4-(4-Acetyl-3-hydroxy-2-propylphenoxy)butanoic acid was allowed to react with 3-pyridine propanamine according to procedure A and the product was purified by chromatography on silica gel to give 4-(4-acetyl-3-hydroxy-2-propylphenoxy)-N-[3-(3-pyridinyl)propyl]-butanamide, the title compound, mp 97°–98° (from methylene chloride-ether) in 88% yield.

Analysis Calculated for $C_{23}H_{30}N_2O_4$: C, 69.32; H, 7.59; N, 7.03. Found: C, 69.03; H, 7.71; N, 6.90.

EXAMPLE 13

Preparation of
4-(4-Acetyl-3-hydroxy-2-propylphenoxy)-N-[2-(3-pyridinyl)ethyl]butanamide 4-(4-Acetyl-3-hydroxy-2-propylphenoxy)butanoic acid was allowed to react with 3-pyridine ethanamine according to procedure A and the product was purified by chromatography on silica gel to give 4-(4-acetyl-3-hydroxy-2-propylphenoxy)-N-[2(3-pyridinyl)ethyl]-butanamide, the title compound, mp 94°–96° (from methylene chloride-ether) in 74% yield.

Analysis Calculated for $C_{22}H_{28}N_2O_4$: C, 68.73; H, 7.34; N, 7.29. Found: C, 68.50; H, 7.24; N, 7.28.

EXAMPLE 14

Preparation of
6-(4-Acetyl-3-hydroxy-2-propylphenoxy)-N-[4-(1H-imidazol-1-yl)butyl]-hexanamide semihydrate 6-(4-Acetyl-3-hydroxy-2-propylphenoxy)hexanoic acid was allowed to react with I-H-imidazloe-1-butanamine according to procedure A and the product was purified by chromatography on silica gel to give 6-(4-acetyl-3-hydroxy-2-propylphenoxy)-N-[4-(1H-imidazol-1-yl)butyl]-hexanamide semihydrate, the title compound as an oil in 44% yield.

Analysis Calculated for $C_{24}H_{35}N_3O_4$ 0.5 $H_2O$: C, 65.82; H, 8.27; N, 9.58; $H_2O$, 2.05. Found: C, 65.86; H, 8.29; N, 9.83; $H_2O$, 2.13.

EXAMPLE 15

Preparation of
6-(4-Acetyl-3-hydroxy-2-propylphenoxy)-N-[4-(2-pyridinyl)butyl]hexanamide 6-(4-Acetyl-3-hydroxy-2-propylphenoxy)hexanoic acid was allowed to react with 2-pyridine butanamine according to procedure A and the product was purified by crystallization from ether-hexane to give 6-(4-acetyl-3-hydroxy-2-propylphenoxy)-N-[4-(2-pyridinyl)butyl]-hexanamide, the title compound, mp 63°–66° in 76% yield.

Analysis Calculated for $C_{26}H_{36}N_2O_4$: C, 70.88; H, 8.24; N, 6.36. Found: C, 70.63; 8.08; N, 6.45.

EXAMPLE 16

Preparation of
6-(4-Acetyl-3-hydroxy-2-propylphenoxy)-N-[4-(5-pyrimidinyl)butyl]hexanamide 6-(4-Acetyl-3-hydroxy-2-propylphenoxy)hexanoic acid was allowed to react with 5-pyrimidine butanamine according to procedure A and the product was purified by crystallization from carbon tetrachloride to give 6-(4-acetyl-3-hydroxy-2-propylphenoxy)-N-[4-(5-pyrimidinyl)-butyl]hexanamide, the title compound mp 87°–89°, in 73% yield.

Analysis Calculated for $C_{25}H_{35}N_3O_4$: C, 68.00; H, 7.99; N, 9.52. Found: C, 68.03; H, 8.10; N, 9.58

EXAMPLE 17

Preparation of
6-(4-Acetyl-3-hydroxy-2-propylphenoxy)-N-[2-(4-pyridinylthio)ethyl]hexanamide 6-(4-Acetyl-3-hydroxy-2-propylphenoxy)hexanoic acid was allowed to react with 2-(4-pyridinylthio)ethyl amine according to procedure A and the product was purified by crystallization from ethyl acetate-hexane to give 6-(4-acetyl-3-hydroxy-2-propylphenoxy)-N-[2-(4-pyridinylthio)ethyl]hexanamide, the title compound, mp 63°–65°, in 52% yield.

Analysis Calculated for $C_{24}H_{32}N_2O_4S$: C, 64.84; H, 7.26; N, 6.30; S, 7.21. Found: C, 64.60; H, 7.16; N, 2.26; S, 7.15.

EXAMPLE 18

Preparation of
6-(4-Acetyl-3-hydroxy-2-propylphenoxy)-N-[4-(3-pyrindinyloxy)butyl]hexanamide 6-(4-Acetyl-3-hydroxy-2-propylphenoxy)hexanoic acid was allowed to react with 4-(3-pyridinyloxy)butyl amine according to procedure A and the product was purified by HPLC to give 6-(4-acetyl-3-hydroxy-2-propylphenoxy)-N-[4-(3-pyridinyloxy)butyl]hexanamide, the title compound, mp 50°–53° (from ethyl acetate) in 73% yield.

Analysis Calculated for $C_{26}H_{36}N_2O_5$: C, 68.40; H, 7.95; N, 6.14. Found: C, 68.15; H, 7.71; N, 6.23.

EXAMPLE 19

Preparation of
6-(4-Acetyl-3-hydroxy-2-propylphenoxy)-N-[2-(4-pyridinyl)ethyl]hexanamide 6-(4-Acetyl-3-hydroxy-2-propylphenoxy)hexanoic acid was allowed to react with 4-pyridine ethanamine according to procedure A and the product was purified by chromatography on silica gel to give 6-(4-acetyl-3-hydroxy-2-propylphenoxy)-N-[2-(4-pyridinyl)ethyl]-hexanamide, the title compound, mp 80°–83° (from methylene chloride-ether) in 58% yield.

Analysis Calculated for $C_{24}H_{32}N_2O_4$: C, 69.88; H, 7.82; N, 6.79. Found: C, 69.68; H, 7.63; N, 6.80.

EXAMPLE 20

Preparation of
7-(4-Acetyl-3-hydroxy-2-propylphenoxy)-N-[4-(3-pyridinyl)butyl]-5-heptynamide 7-(4-Acetyl-3-hydroxy-2-propylphenoxy)-5-heptynoic acid was allowed to react with 3-pyridine butanamine according to procedure A and the product was purified by HPLC to give 7-(4-acetyl-3-hydroxy-2-propylphenoxy)-N-[4-(3-pyridinyl)butyl]-5-heptynamide, the title compound, mp 77°–80° (from ethyl acetate-hexane) in 53% yield.

Analysis Calculated for $C_{27}H_{34}N_2O_4$: C, 71.97; H, 7.61; N, 6.22. Found: C 72.23; H, 7.79; N, 6.14.

EXAMPLE 21

Preparation of
6-(4-Acetyl-3-hydroxy-2-propylphenoxy)-N-[4-(3-pyridinyl)butyl]-2-hexynamide 6-(4-Acetyl-3-hydroxy-2-propylphenoxy)-2-hexynoic acid was allowed to react with 3-pyridine butanamine according to procedure B and the product was purified by chromatography on silica gel to give 6-(4-acetyl-3-hydroxy-2-propylphenoxy)-N-[4-(3-pyridinyl)butyl]-2-hexynamide, the title compound, mp 84°–86° (from hexane) in 42% yield.

Analysis Calculated for $C_{26}H_{32}N_2O_4$: C, 71.53; H, 7.39; N, 6.42. Found: C, 71.35; H, 7.41; N, 6.33.

EXAMPLE 22

Preparation of
4-(4-Acetyl-3-hydroxy-2-propylphenoxy)-2-methyl-N-[4-(3-pyridinyl)butyl]butanamide 4-(4-Acetyl-3-hydroxy-2-propylphenoxy)-2-methyl butanoic acid was allowed to react with 3-pyridine butanamine according to procedure A and the product was purified by HPLC to give 4-(4-acetyl-3-hydroxy-2-propylphenoxy)-2-methyl-N-[4-(3-pyridinyl)butyl]-butanamide, the title compound as an oil in 89% yield.

Analysis Calculated for $C_{25}H_{34}N_2O_4$: C, 70.40; H, 8.03; N, 6.57. Found: C, 70.17; H, 8.19; N, 6.53.

EXAMPLE 23

Preparation of
4-(4-Acetyl-3-hydroxy-2-propylphenoxy)-3-methyl-N-[4-(3-pyridinyl)butyl]butanamide 4-(4-Acetyl-3-hydroxy-2-propylphenoxy)-3-methyl butanoic acid was allowed to react with 3-pyridinebutanamine according to procedure A and the product was purified by HPLC to give 4-(4-acetyl-3-hydroxy-2-propylphenoxy)-3-methyl-N-[4-(3-pyridinyl)butyl]-butanamide, the title compound, mp 58°–60° (from ethyl acetate-hexane) in 84% yield.

Analysis Calculated for $C_{25}H_{34}N_2O_4$: C, 70.40; H, 8.03; N, 6.57. Found: C, 70.20; H, 8.01; N, 6.41.

EXAMPLE 24

Preparation of
4-(4-Acetyl-3-hydroxy-2-propylphenoxy)-2,2-dimethyl-N-[4-(3-pyridinyl)butyl]butanamide 4(4-Acetyl-3-hydroxy-2-propylphenoxy)-2,2-dimethyl butanoic acid was allowed to react with 3-pyridine butanamine according to procedure A and the product was purified by HPLC to give 4-(4-acetyl-3-hydroxy-2-propylphenoxy)-2,2-dimethyl-N-[4-(3-pyridinyl)butyl]-butanamide, the title compound, mp 80°–83° (from hexane) in 83% yield.

Analysis Calculated for $C_{26}H_{36}N_2O_4$: C, 70.80; H, 8.24; N, 6.36. Found: C, 71.09; H, 8.29; N, 6.39.

EXAMPLE 25

Preparation of
6-(4-Acetyl-3-hydroxy-2-propylphenoxy)-N-
[1methyl-4-(3-pyridinyl)butyl]hexanamide 6-(4Acetyl-3-hydroxy-2-propylphenoxy)hexanoic acid was allowed to react with 1-methyl-3-pyridine butanamine according to procedure A and the product was purified by chromatography on silica gel to give 6-(4-acetyl-3-hydroxy-2-propylphenoxy)-N-[1-methyl-4-(3-pyridinyl)butyl]- hexanamide, the title compound, mp 63°–66° (from ethyl acetate-hexane) in 76% yield.

Analysis Calculated for $C_{27}H_{38}N_2O_4$: C, 71.34; H, 8.43; N, 6.16. Found: C, 71.26; H, 8.43; N, 6.16.

EXAMPLE 26

Preparation of
4-(4-Acetyl-3-hydroxy-2-propylphenoxy)-3-methyl-N-
[1-methyl-4-(3-pyridinyl)butyl]-butanamide 4-(4-(Acetyl-3hydroxy-2-propylphenoxy)-3-methyl butanoic acid was allowed to react with 1-methyl-3-pyridine butanamine according to procedure A and the product was purified by chromatography on silica gel to give (4-acetyl-3-hydroxy-2-propylphenoxy)-3-methyl-N-[1-methyl-4-(3-pyridinyl)butyl]-butanamide, the title compound, mp 77°–83°, in 73% yield.

Analysis Calculated for $C_{26}H_{36}N_2O_4$: C, 70.88; H, 8.24; N, 6.36. Found: C, 70.96; H, 8.31; N, 6.48.

EXAMPLE 27

Preparation of
4-(4-Acetyl-3-hydroxy-2-propylphenoxy)-N-[1-methyl-
4-(3-pyridinyl)butyl]butanamide 4-(4-Acetyl-3-hydroxy-2-propylphenoxy)butanoic acid was allowed to react with 1-methyl-3-pyridine butanamine according to procedure A and the product was purified by chromatography on silica gel to give 4-(4-acetyl-3-hydroxy-2-propylphenoxy)-N-[1-methyl-4-(3-pyridinyl)butyl]butanamide, the title compound, mp 97°–99°, in 57% yield.

Analysis Calculated for $C_{25}H_{34}N_2O_4$: C, 70.40; H, 8.03; N, 6.57. Found: C, 70.59; H, 8.21; N, 6.70.

EXAMPLE 28

Preparation of
6-(4-Acetyl-3-hydroxy-2-propylphenoxy)-hexanoic
acid, 3-(3-pyridinyl)propyl ester hydrochloride A mixture of 0.308 g of 6-(4-acetyl-3-hydroxy-2-propylphenoxy)hexanoic acid, 0.281 g of 3-(3-pyridinyl)-propyl bromide, 0.415 g of anhydrous potassium carbonate and 0.166 g of potassium iodide in 10 mL of anhydrous dimethyl formamide was stirred and heated at 70° for 1 hour. The solvent was removed in vacuo, the residue was dissolved in methylene chloride, washed with sodium bicarbonate solution and dried over sodium sulfate. Concentration in vacuo gave an oil which was chromatographed on 50 g of silica gel and eluted with ethyl acetate to give 0.42 g of an oil. The hydrochloride salt was crystallized from 2-propanol-ether to give 0.26 g, mp 80°–81° (60% yield) of 6-(4-acetyl-3-hydroxxy-2-propylphenoxy)-hexanoic acid, 3-(3-pyridinyl)propyl ester hydrochloride, the title compound.

Analysis Calculated for $C_{25}H_{33}NO_5HCl$: C, 64.71; H, 7.39; N, 3.02; Cl−, 7.64. Found: C, 64.78; H, 7.35; N, 3.12; Cl−, 7.40.

EXAMPLE 29

Preparation of
N-[5-(4-Acetyl-3-hydroxy-2-propylphenoxy)-pentyl]-
N'-[4-(3-pyridinyl)butyl]urea To a cooled (3) solution of 2.0 g of 6-(4-acetyl-3-hydroxy-2-propylphenoxy)hexanoic acid in 40 mL of anhydrous toluene was added 1.68 mL of diphenylphosphoryl azide followed by 1.36 mL of triethyl amine. The mixture was stirred at 3° for 90 minutes and at 90° for 5 hours. After cooling, 1.07 g of 3-pyridine butanamine was added and heating at 90° was continued for 24 hours. The solvent was removed in vacuo and the residual oil was dissolved in methylene chloride and washed with sodium bicarbonate solution. The dried (over magnesium sulfate) extract was concentrated and purified by HPLC using 7% methanol-ethyl acetate. Crystallization of the combined pure fractions from ethyl acetate-hexane gave 2.0 g, mp 73°–76° (66% yield) of N-[5-(4-acetyl-3-hydroxy-2-propylphenoxy)-pentyl]-N'-[4-(3-pyridinyl)-butyl]urea Analysis Calculated for $C_{24}H_{33}N_3O_4$: C, 68.54; H, 8.19; N, 9.22. Found: C, 68.54; H, 8.25; N, 9.26.

EXAMPLE 30

Preparation of
N-[3-(4-Acetyl-3-hydroxy-2propylphenoxy)-propyl]-
N'-[4-(3-pyridinyl)butyl]urea To a cooled (3°) solution of
2.0 g of
4-(4-acetyl-3-hydroxy-2-propylphenoxy)butanoic acid in 40 mL of anhydrous toluene was added 1.85 mL of diphenylphosphoryl azide followed by 1.50 mL of triethylamine. The mixture was stirred at 3° for 90 minutes and at 90° for 5 hours. After cooling, 1.17 g of 3-pyridine butanamine was added and heating at 90° was continued for 24 hours. The solvent was removed in vacuo and the residual oil was dissolved in methylene chloride and washed with sodium bicarbonate solution. The dried (over magnesium sulfate) extract was concentrated and purified by HPLC using a 8% methanol: 2% triethylamine; ethyl acetate. Crystallization of the combined pure fractions from ethyl acetate-hexane gave 2.0 g, mp 73°–76° (66% yield) of N-[3-(4-acetyl-3-hydroxy-2-propylphenoxy)-propyl]-N'-[4-(3-pyridinyl)butyl]urea, the title compound.

Analysis Calculated for $C_{24}H_{33}N_3O_4$: C, 67.42; H, 7.78; N, 9.83. Found: C, 67.40; H, 7.50; N, 9.79.

EXAMPLE 31

Preparation of
4-[(4-Acetyl-3-hydroxy-2-propylphenoxy)-methyl]-N-
[4-(3-pyridinyl)butyl]benzamide To a stirred solution of 1.50 g of 4-[(4-acetyl-3-hydroxy-2-propylphenoxy)methyl] benzoic acid and 0.756 g of 3-pyridine butanamine in 10 mL of anhydrous DMF (dimethylformamide) cooled at −5°, was added dropwise 1.10 mL of diphenylphosphoryl azide followed by the dropwise addition of 1.35 mL of triethylamine. The reaction mixture was stirred at −5° for 3 hours and then at 25° for 16 hours. The DMF was removed in vacuo and methylene chloride was added to the residue. The solution was washed with saturated sodium biocarbonate solution, washed with saturated sodium chloride solution, dried over magnesium sulfate and concentrated in vacuo. Chromatography of the resultant oil on 150 g of silica gel and elution with a solvent mixture of methylene chloride (90): 95% methanol (10): Conc, ammonium hydroxide (0.25) gave 1.35 g of an oil. Crystallization from acetone-hexane gave 1.06 g, mp 91°–95°, (50% yield) of 4-[(4-Acetyl-3-hydroxy-2-propylphenoxy)-methyl]-N-[4-(3-pyridinyl)butyl]benzamide, the title compound.

Analysis Calculated for $C_{28}H_{32}N_2O_4$: C, 73.02; H, 7.00; N, 6.08. Found: C, 71.71; H, 7.25; N, 6.10.

EXAMPLE 32

Preparation of 3-[(4-Acetyl-3-hydroxy-2-propylphenoxy)-methyl]-N-[4-(3-pyridinyl)butyl]benzamide To a stirred solution of 1.50 g of 3-[(4-acetyl-3-hydroxy-2-propylphenoxy)methyl]benzoic acid dissolved in 30 mL anhydrous DMF cooled to −5° was added dropwise 1.10 mL of diphenylphosphoryl azide followed by the dropwise addition of 1.35 mL of triethylamine. After stirring at −5° for 10 minutes, a white solid crystallized out. Stirring was continued for 1.5 hours. The reaction mixture was then warmed to 5° and 0.756 g of 3-pyridine butanamine was added dropwise. The resulting yellow solution was stirred at 5° for 4 hours and then at 25° for 17 hours. The DMF was removed in vacuo and methylene chloride was added to the residue. The solution was washed with saturated sodium bicarbonate, washed with sodium chloride, dried (over magnesium sulfate) and concentrated in vacuo to a solid. Chromatography of this solid on 120 g of silica gel and elution with a solvent mixture of methylene chloride (90): 95% methanol (10): Conc ammonium hydroxide (0.25) gave a solid. Recrystallization from methylene chloride-ether gave 1.79 g, mp 120°–123°, (85%) of 3-[(4-Acetyl-3- hydroxy-2-propylphenoxy)-methyl]-N-[4-(3-pyridinyl)butyl]benzamide, the title compound.

Analysis Calculated for $C_{28}H_{32}N_2O_4$: C, 73.02; H, 7.00; N, 6.08. Found: C, 73.32; H, 7.14; N, 6.11.

EXAMPLE 33

Preparation of 2-[(4-Acetyl-3-hydroxy-2-propylphenoxy)-methyl]-N-[4-(3-pyridinyl)butyl]benzamide 2-[(4-Acetyl-3-hydroxy-2-propylphenoxy)methyl]benzoic acid was allowed to react with 3-pyridine butanamine according to the procedure of Example 32 and the product was purified by recrystallization from methylene chloride-ether to give, 2-[(4-Acetyl-3-hydroxy-2-propylphenoxy)-methyl]-N-[4-(3-pyridinyl)-butyl]benzamide, the title compound, mp 135°–139° in 87% yield.

Analysis Calculated for $C_{28}H_{32}N_2O_4$: C, 73.02; H, 7.00; N, 6.08. Found: C, 72.66; H, 6.83; N, 5.93.

EXAMPLE 34

Preparation of 4-[(4-Acetyl-3-hydroxy-2-propylphenoxy)-methyl]-N-[1-methyl-4-(3-pyridinyl)butyl]benzamide 4-[(4-Acetyl-3-hydroxy-2-propylphenoxy)methyl]benzoic acid was allowed to react with 1-methyl-3-pyridine butanamine according to the procedure of Example 32 and the produce was purified by column chromotography to give, 4-[(4-Acetyl-3-hydroxy-2-propylphenoxy)-methyl]-N-[1-methyl-4-(3-pyridinyl)butyl]benzamide, the title compound, mp 117°–120° (from methylene chloride-ether) in 69% yield.

Analysis Calculated for $C_{29}H_{34}N_2O_4$: C, 73.39; H, 7.22; N, 5.90. Found: C, 73.56; H, 7.42; N, 5.98.

EXAMPLE 35

Preparation of 3-[(4-Acetyl-3-hydroxy-2-propylphenoxy)-methyl]-N-[1-methyl-4-(3-pyridinyl)butyl]benzamide 3-[(4-Acetyl-3-hydroxy-2-propylphenoxy)methyl]-benzoic acid was to react with 1-methyl-3-pyridine butanamine according to the procedure of Example 32 and the product was purified by column chromotography to give, 3-[(4-Acetyl-3-hydroxy-2-propylphenoxy)-methyl]-N-[1-methyl-4-(3-pyridinyl)butyl]benzamide, the title compound, mp 115°–118° (from methylene chloride-ether) in 69% yield.

Analysis Calculated for $C_{29}H_{34}N_2O_4$: C, 73.39; H, 7.22; N, 5.90. Found: C, 73.48; H, 7.57; N, 5.97.

EXAMPLE 36

Preparation of 3-[(4-Acetyl-3-hydroxy-2-propylphenoxy)-methyl]-2-ethoxy-[4-(3-pyridinyl)butyl]benzamide 3-[(4-Acetyl-3-hydroxy-2-propylphenoxy)methyl]-2-ethoxybenzoic acid was allowed to react with 3-pyridine butanamine according to the procedure of Example 32 and the product was purified by recrystallization from methylene chloride-ether to give, 3-[(4-Acetyl-3-hydroxy-2-propylphenoxy-methyl]-2-ethoxy-[4-(3-pyridinyl)butyl]benzamide, the title compound, mp 107°–109° in 73% yield.

Analysis Calculated for $C_{30}H_{36}N_2O_5$: C, 71.41; H, 7.19; N, 5.55. Found: C, 71.13; H, 7.23; N, 5.51.

EXAMPLE 37

Preparation of 4-[(4-Acetyl-3-hydroxy-2-propylphenoxy)-methyl]-2-ethoxy-N-[4-(3-pyridinyl)butyl]benzamide 4[-(4-Acetyl-3-hydroxy-2-propylphenoxy)methyl]-2-ethoxybenzoic acid was allowed to react with 3-pyridine butanamine according to the procedure of Example 32 and the product was purified by recrystallization from methylene chloride-ether to give, 4-[(4-Acetyl-3hydroxy-2-propylphenoxy)methyl]-2-ethoxy-N-[4-(3-pyridinyl)butyl]benzamide, the title compound, mp 92°–93° in 69% yield.

Analysis Calculated for $C_{30}H_{36}N_2O_5$: C, 71.41; H, 7.19; N, 5.55. Found: C, 71.69; H, 7.16; N, 5.61.

EXAMPLE 38

Preparation of 3-[(4-Acetyl-3-hydroxy-2-propylphenoxy)-methyl]-N-[3-(3-pyridinyl)propyl]benzamide 3-[(4-Acetyl-3-hydroxy-2-propylphenoxy)methyl]-benzoic acid was allowed to react with 3-pyridine propanamine according to the procedure of Example 32 and the product was purified by recrystallization from acetone-hexane to give, 3-[(4-Acetyl-3-hydroxy-2-propylphenoxy)methyl]-N-[3-(3-pyridinyl)propyl]benzamide, the title compound, mp 110°–112° in 90% yield.

Analysis Calculated for $C_{27}H_{30}N_2O_4$: C, 72.62; H, 6.77; N, 6.27. Found: C, 72.50; H, 6.71; N, 6.13.

EXAMPLE 39

Preparation of
N'-[3-[(4-Acetyl-3-hydroxy-2-propylphenoxy)-methyl]-phenyl]-N-[4-(3-pyridinyl)butyl]]urea To a stirred solution of 0.986 g of 3-[(4-Acetyl-3-hydroxy-2-propylphenoxy)methyl]benzoic acid dissolved in 10 mL anhydrous DMF and 10 mL anhydrous toluene cooled to 5° was added dropwise 0.78 mL of diphenylphosphoryl azide followed by the dropwise addition of 0.89 mL of triethylamine. After stirring at 5° for 1.5 hours and heating at 90° for 5 hours, the reaction mixture was cooled to 25° and 0.497 g of 3-pyridine butanamine was added dropwise. The resulting yellow solution was heated at 90° for 24 hours and the solvents were removed in vacuo. The residue was dissolved in ethyl acetate and washed with saturated sodium bicarbonate, dried over magnesium sulfate and concentrated in vacuo to an oil which was purified by HPLC. Elution with triethylamine (3): methanol (5); ethyl acetate (92) gave a solid which was recrystallized from acetone-hexane. Filtration gave 0.313 g, mp 141°–143°, (22% yield) of N'-[3-[(4-Acetyl-3-hydroxy-2-propylphenoxy)methyl]phenyl]- N-[4-(3-pyridinyl)butyl]]urea, the title compound.

Analysis Calculated for $C_{28}H_{33}N_3O_4$: C, 70.71; H, 6.99; N, 8.84. Found: C, 70.50; H, 6.92; N, 8.72.

EXAMPLE 40

Preparation of
4-[2-(4-Acetyl-3-hydroxy-2-propylphenoxy)-ethoxy]-N-[4-(3-pyridinyl)butyl]benzamide To a cold (0° C.) solution of 1.22 g of 4-[2-(4-Acetyl-3-hydroxy-2-propylphenoxy)ethoxy]benzoic acid in 15 mL of anhydrous DMF was added to 0.8 mL of diphenylphosphoryl azide and 1.05 mL of anhydrous triethylamine. The resulting mixture was stirred at 0° C. for one hour and then 0.56 g of 3-pyridine butanamine was added. The mixture was stirred in ice bath for 1 hour and at room temperature for 6 hours. The solvent was removed in vacuo, the residue was dissolved in methylene chloride and washed with sodium bicarbonate solution. The extract was dried (over magnesium sulfate) and concentrated in vacuo to an oil which was purified by HPLC using 7% methanol-ethyl acetate to give an oil which was triturated with ethyl acetate-ether and filtered to yield 1.0 g, mp 93°, (60% yield) of 4-[2-(4-Acetyl-3-hydroxy-2-propylphenoxy)-ethoxy]-N-[4-(3-pyridinyl)butyl]benzamide, the title compound.

Analysis Calculated for $C_{29}H_{34}N_2O_5$: C, 71.00; H, 6.99; N, 5.71. Found: C, 70.70; H, 6.99; N, 5.97.

EXAMPLE 41

Preparation of
3-[2-(4-Acetyl-3-hydroxy-2-propylphenoxy)-ethoxy]-N-84-(3-pyridinyl)butyl]benzamide The reaction of 1.06 g of 3-[2-(4-acetyl-3hydroxy-2propylphenoxy)ethoxy]benzoic acid with 0.49 g of 3-pyridine butanamine according to Example 40 gave 1.20 g, mp 90°, (83% yield) of 3-[2-(4-Acetyl-3-hydroxy-2-propylphenoxy)ethoxy]-N-[4-(3-pyridinyl)-butyl]benzamide, the title compound.

Analysis Calculated for $C_{29}H_{34}N_2O_5$: C, 71.00; H, 6.99; N, 5.71. Found: C, 70.71; H, 6.86; N, 5.65.

EXAMPLE 42

Preparation of
2-[2-(4-Acetyl-3-hydroxy-2propylphenoxy)-ethoxy]-N-8 4-(3-pyridinyl)butyl]benzamide The reaction of 0.83 g of 2-[2-(4-acetyl-3-hydroxy-2-propylphenoxy)ethoxy]benzoic acid with 0.38 g (0.0026 mol) of 3-pyridine butanamine according to Example 40 gave 0.88 g, mp 77°–80°, (77% yield) of 2-[2-(4-Acetyl-3-hydroxy-2-propylphenoxy)ethoxy]-N-[4-(3-pyridinyl)butyl]benzamide, the title compound.

Analysis Calculated for $C_{29}H_{34}N_2O_5$: C, 71.00; H, 6.99; N, 5.71. Found: C, 71.04; H, 6.98; N, 5.68.

EXAMPLE 43

Preparation of
3-[3-(4-Acetyl-3-hydroxy-2propylphenoxy)-propoxy]-N-[4-(3-pyridinyl)butyl]benzamide The reaction of 0.80 g of 3-[3-(4-acetyl-3-hydroxy-2-propylphenoxy)propoxy]benzoic acid with 0.35 g of 3-pyridine butanamine according to Example 40 gave 0.95 g, mp 84°–86°, (88% yield) of 3-[3-(4-Acetyl-3-hydroxy-2-propylphenoxy)propoxy]-N-[4-(3-pyridinyl)butyl]benzamide, the title compound.

Analysis Calculated for $C_{29}H_{34}N_2O_5$: C, 71.00; H, 6.99; N, 5.71. Found: C, 71.52; H, 7.36; N, 5.60.

EXAMPLE 44

Preparation of
2-[3-(4-Acetyl-3-hydroxy-2-propylphenoxy)-propoxy]-N-[4-(3-pyridinyl)butyl]benzamide The reaction of 0.79 g of 2-[3-(4-acetyl-3hydroxy-2-propylphenoxy)propoxy]benzoic acid with 0.35 g of 3-pyridine butanamine according to Example 40 gave 0.70 g, mp 104°–107°, (65% yield) of 2-[3-(4-Acetyl-3-hydroxy-2-propylphenoxy)propoxy]-N-[4-(3-pyridinyl)butyl]benzamide, the title compound.

Analysis Calculated for $C_{29}H_{34}N_2O_5$: C, 71.00; H, 6.99; N, 5.71. Found: C, 71.25; H, 7.23; N, 5.55.

EXAMPLE 45

Preparation of
4-[3(4-Acetyl-3-hydroxy-2propylphenoxy)-propoxy]-N-[4-(3-pyridinyl)butyl]benzamide The reaction of 0.635 g of 4-[3-(4-acetyl-3-hydroxy-2-propylphenoxy)propoxy]benzoic acid with 0.28 g of 3-pyridine butanamine according to Example 40 gave 0.80 g, mp 133°–134°, (93% yield) of 4-[3-(4-Acetyl-3-hydroxy-2-propylphenoxy)propoxy]-N-[4-(3-pyridinyl)butyl]benzamide, the title compound.

Analysis Calculated for $C_{29}H_{34}N_2O_5$: C, 71.00; H, 6.99; N, 5.71. Found: C, 71.35; H, 7.36; N, 5.54.

EXAMPLE 46

Preparation of
(4-Acetyl-3-hydroxy-2-propylphenoxy)acetic acid ethyl ester.

A mixture of 24.25 g of 1-(2,4-dihydroxy-3-propylphenyl) ethanone, 16.0 ml of ethyl chloroacetate and 26 g of anhydrous potassium carbonate in 375 ml of anhydrous acetone was stirred at reflux for 17 hours. The reaction mixture was filtered and the filtrate was concentrated in vacuo to an oil which was crystallized from ethanol to give 27.2 g of (4-acetyl-3-hydroxy-2-propylphenoxy)acetic acid, the titled compound, mp 61°–64°, (78% yield) in two crops.

Analysis Calculated for $C_{15}H_{20}O_5$: C, 64.27; H, 7.19.
Found: C, 64.10; H, 7.12.

EXAMPLE 47

Preparation of
(4-Acetyl-3-hydroxy-2-propylphenoxy)acetic

To 5.6 g of (4-acetyl-3-hydroxy-2-propylphenoxy)acetic acid ethyl ester in 50 ml of methanol was added 50 ml of 1.0N sodium hydroxide and the solution was stirred at reflux for 2 hours. The methanol was removed in vacuo, the residue was acidified and the product was extracted with ether. The dried (over magnesium sulfate) extract was concentrated *in vacuo* to a solid which was recrystallized from ether-hexane to give 4.18 g of (4-acetyl-3-hydroxy-2-propylphenoxy)acetic acid, the titled compound, mp 128°–130°, (83% yield).

EXAMPLE 48

Preparation of
1-[2-Hydroxy-4-(3-hydroxypropoxy)-3-propyl-phenyl]ethanone

A mixture of 5.80 g of 1-(2,4-dihydroxy-3-propylphenyl) ethanone, 3.6 ml of 3-bromo-1-propanol and 8.3 g of anhydrous potassium carbonate in 50 ml of anhydrous dimethyl formamide was stirred at 75° for 64 hours. The reaction mixture was concentrated in vacuo, the residue was acidified and extracted with ethyl acetate. The extract was dried over magnesium sulfate and concentrated in vacuo to 8.7 g of an oil which was chroma,ographed on 150 g of silica gel. Elution with 40% ethyl acetate-toluene gave 2.84 g which was crystallized from ether-hexane to yield 2.14 g, mp 57–59°, (28% yield) of 1-[2-hydroxy-4-(3-hydroxypropoxy)-3-propyl-phenyl]ethanone, the titled compound.

Analysis Calculated for $C_{14}H_{20}O_4$: C, 66.65; H, 7.99.
Found: C, 66.56; H, 7.99.

Additonal fractions (1.42 g) of slightly impure product were obtained.

EXAMPLE 49

Preparation of
3-(4-Acetyl-3-hydroxy-2-propylphenoxy) propanoic acid

A solution of 2.00 g of 1-[2-hydroxy-4-(3-hydroxypropoxy)-3-propylphenyl]ethanone in 30 ml of acetone was added dropwise over 45 minutes to a stirred, ice cooled solution of 4.0 ml of Jones reagent in 10 ml of acetone. After 15 additional minutes, the cooling bath was removed and the reaction mixture was stirred at 23° for 15 minutes. Jones reagent (0.5 ml) was added and stirring was continued for 15 minutes. The reaction mixture was concentrated in vacuo and the residue was treated with water and extracted with ether. The ether extract was washed with three portions of 1N sodium hydroxide and the aqueous layers were combined and acidified. The product was extracted with ether and the dried (over magnesium sulfate) extract was concentrated in vacuo to a solid (1.48 g). Recrystallization from ether-hexane gave 1.21 g, mp 142°–146°, (57% yield) of 3-(4-acetyl-3hydroxy-2-propylphenoxy)-propanoic acid, the titled compound.

Analysis Calculated for $C_{14}H_{18}O_5$: C, 63.15; H, 6.81.
Found: C, 62.95; H, 7.01.

EXAMPLE 50

Preparation of
4-(4-Acetyl-3-hydroxy-2-propylphenoxy) butanoic acid ethyl ester.

A mixture of 2.91 g of 1-(2,4-dihydroxy-3-propylphenyl) ethanone, 2.91 g of ethyl 4-bromobutyrate and 3.1 g of anhydrous potassium carbonate in 35 ml of anhydrous dimethyl formamide was stirred and heated at 75° for 12 hours. The solvent was removed in vacuo, the residue was treated with water and the product was extracted with ethyl acetate. The dried (over magnesium sulfate) extract was concentrated in vacuo and the crude product was purified by chromatography on 200 g of silica gel. Elution with 5% ethyl acetate-toluene gave 2.55 g (54% yield) of 4-(4-acetyl-3-hydroxy-2-propylphenoxy) butanoic acid ethyl ester, the titled compound, as an oil.

Analysis Calculated for $C_{17}H_{24}O_5$: C, 66.21; H, 7.84.
Found: C, 66.33; H, 8.00.

EXAMPLE 51

Preparation of
4-(4-Acetyl-3-hydroxy-2-propylphenoxy) butanoic acid

A solution of 2.45 g of 4-(4-acetyl-3-hydroxy-2-propylphenoxy)butanoic acid ethyl ester in 40 ml of methanol and 40 ml of 1.0N sodium hydroxide was heated at reflux for 10 minutes. The methanol was removed in vacuo, the residue was acidified and the product was extracted with ether. The dried (over magnesium sulfate) extract was concentrated in vacuo and the solid residue was recrystallized from ether-hexane to give 1.95 g (87% yield), mp 130°–133°, of 4-(4-acetyl-3-hydroxy-2-propylphenoxy) butanoic acid, the titled compound.

Analysis Calculated for $C_{15}H_{20}O_5$: C, 64.27; H, 7.19.
Found: C, 64.09; H, 7.38.

EXAMPLE 52

Preparation of
5-(4-Acetyl-3-hydroxy-2-propylphenoxy) pentanoic acid methyl ester A mixture of 2.92 g of 1-(2,4-dihydroxy-3-propylphenyl) ethanone, 2.91 g of methyl 5-bromopentanoate and 3.1 g of anhydrous potassium carbonate in 35 ml of anhydrous dimethyl formamide was stirred and heated at 75° for 16 hours. The usual workup followed by chromatography on 350 g of silica gel and elution with 5% ethyl acetate-toluene gave 3.07 g (66% yield) of 5-(4-Acetyl-3-hydroxy-2-propylphenoxy) pentanoic acid methyl ester, the titled compound, as an oil.

Analysis Calculated for $C_{17}H_{24}O_5$: C, 66.21; H, 7.85.
Found: C, 66.39; H, 7.80.

EXAMPLE 53

Preparation of
5-(4-Acetyl-3-hydroxy-2-propylphenoxy) pentanoic acid

A solution of 2.97 g of 5-(4-acetyl-3-hydroxy-2-propylphenoxy) pentanoic acid methyl ester in 50 ml of methanol and 50 ml of 1.0 N sodium hydroxide was heated at reflux for 10 minutes. The usual workup followed by recrystallization from ether-hexane gave 2.69 g (95% yield), mp 97°–102°, of 5-(4-Acetyl-3-hydroxy-2-propyl-phenoxy) pentanoic acid, the titled compound.

Analysis Calculated for $C_{16}H_{22}O_5$: C, 65.29; H, 7.53. Found: C, 65.46; H, 7.77.

EXAMPLE 54

Preparation of 6-(4-Acetyl-3-hydroxy-2-propylphenoxy) hexanoic acid methyl ester A mixture of 2.72 g of 1-(2,4-dihydroxy-3-propylphenyl) ethanone, 2.72 g of methyl 6-bromohexanoate and 2.90 g of anhydrous potassium carbonate in 30 ml of anhydrous dimethyl formamide was stirred and heated at 75° for 7 hours. The usual workup followed by chromatography on 200 g of silica gel and elution with 10% ethyl acetate-toluene gave 2.77 g (62% yield) of 6-(4-Acetyl-3-hydroxy-2-propylphenoxy) hexanoic acid methyl ester, the titled compound, as an oil.

Analysis Calculated for $C_{18}H_{26}O_5$: C, 67.06; H, 8.13. Found: C, 66.92; H, 8.25.

EXAMPLE 55

Preparation of 6-(4-Acetyl-3-hydroxy-2-propylphenoxy) hexanoic acid

A solution of 1.40 g of 6-(4-acetyl-3-hydroxy-2-propylphenoxy) hexanoic acid methyl ester in 20 ml of methanol and 22 ml of 1.0 N sodium hydroxide was stirred at reflux for 10 minutes. The usual workup followed by recrystallization from ether-hexane gave 1.10 g (82%) yield), mp 62°-64°, of 6-(4-acetyl-3-hydroxy-2-propylphenoxy) hexanoic acid, the titled compound.

Analysis Calculated for $C_{17}H_{24}O_5$: C, 66.21; H, 7.84. Found: C, 65.97; H, 7.95.

EXAMPLE 56

Preparation of 8-(4-Acetyl-3-hydroxy-2-propylphenoxy) octanoic acid methyl ester A mixture of 4.30 g of 1-(2,4-dihydroxy-3-propylphenyl) ethanone, 5.10 g of methyl 8-bromooctanoate and 4.55 g of anhydrous potassium carbonate in 100 ml of anhydrous acetone and 30 ml of anhydrous dimethyl formamide was stirred at reflux for 20 hours. The usual workup followed by purification by high pressure liquid chromatography using a solvent of 15% ethyl acetate-hexane gave 4.5 g (58% yield) of 8-(4-acetyl-3-hydroxy-2-propylphenoxy) octanoic acid methyl ester, the titled compound, mp 39–41°, after crystallization from hexane.

Analysis Calculated for $C_{20}H_{30}O_5$: C, 68.55; H, 8.63. Found: C, 68.62; H, 8.81.

EXAMPLE 57

Preparation of 8-(4-Acetyl-3-hydroxy-2-propylphenoxy) octanoic acid.

A solution of 4.50 g of 8-(4-acetyl-3-hydroxy-2-propylphenoxy) octanoic acid methyl ester in 60 ml of methanol and 50 ml of 1.0 N sodium hydroxide was refluxed for 7 minutes. The usual workup followed by purification by high pressure liquid chromatography gave 2.3 g (33% yield), mp 73°–76°, of 8-(4-acetyl-3-hydroxy-2-propylphenoxy) octanoic acid, the titled compound.

Analysis Calculated for $C_{19}H_{28}O_5$: C, 67.83; H, 8.39. Found: C, 67.70; H, 8.25.

1.5 g of the starting methyl ester was also recovered in this experiment.

EXAMPLE 58

Preparation of 11-(4-Acetyl-3-hydroxy-2-propylphenoxy) undecanoic acid methyl ester.

A mixture of 1.00 g of 1-(2,4-dihydroxy-3-propylphenyl) ethanone, 1.44 g of methyl 11-bromoundecanoate and 1.00 g of anhydrous potassium carbonate in 20 ml of anhydrous dimethyl formamide was stirred and heated at 75° for 2 hours. The usual workup followed by chromatography on 30 g of silica gel and elution with 10% ethyl acetate-toluene gave 1.48 g (76% yield) of 11-(4-Acetyl-3-hydroxy-2-propylphenoxy) undecanoic acid methyl ester, the titled compound, as an oil.

Analysis Calculated for $C_{23}H_{36}O_5$: C, 70.38; H, 9.24. Found: C, 70.37; H, 9.36.

EXAMPLE 59

Preparation of 11-(4-Acetyl-3-hydroxy-2-propylphenoxy) undecanoic acid

A suspension of 1.38 g of 11-(4-acetyl-3-hydroxy-2-propylphenoxy) undecanoic acid methyl ester in 20 ml of methanol and 18 ml of 1.0 N sodium hydroxide was stirred at 23° for 2 hours and then at reflux for 10 minutes. The usual workup followed by crystallization from ether-hexane gave 1.15 g (87% yield), mp 57°–58°, of 11-(4-acetyl-3-hydroxy-2-propylphenoxy) undecanoic acid, the titled compound.

Analysis Calculated for $C_{22}H_{34}O_5$: C, 69.81; H, 9.05. Found: C, 69.92; H, 9.14.

EXAMPLE 60

Preparation of 1-[2-Hydroxy-4-[(6-hydroxy-4-hexynyl)oxy]-3-propylphenyl]ethanone.

A mixture of 9.77 g of 1-(2,4-dihydroxy-3-propylphenyl) ethanone, 10.90 g of 1-(tetrahydro-2-pyranoxy)-6-chloro-2-hexyne [R. B. Moffet, P. H. Seay and W. R. Reid, J. Med. Pharm. Chem., 14, 1075 (1971)]. 10.43 g of anhydrous potassium carbonate and 8.36 g of potassium iodide in 250 ml of anhydrous acetone was stirred at reflux for 18 hours. Anhydrous dimethyl formamide (100 ml) was added and reflux with stirring was continued for 52 hours. The solvent was removed in vacuo, the residue was stirred with hexane and filtered. The filtrate was concentrated in vacuo to an oil which was dissolved in 300 ml of methanol and 200 ml of 3 N hydrochloric acid and heated on the steam bath for 45 minutes. As the solvent was being removed in vacuo, crystallization occurred. Water was added and the solid was filtered to give 11.78 g, 88°–90°, (81% yield) of 1-[2-hydroxy-4-[(6-hydroxy-4-hexynyl)oxy]-3-propylphenyl]ethanone, the titled compound.

Analysis Calculated for $C_{17}H_{22}O_4$: C, 70.32; H, 7.64. Found: C, 70.18; H, 7.87.

EXAMPLE 61

Preparation of 6-(4-Acetyl-3-hydroxy-2-propylphenoxy)-2-hexynal

To 2.07 g of 1-[2-hydroxy-4-[(6-hydroxy-4-hexynyl)oxy]-3-propylphenyl]ethanone in 150 ml of methylene chloride at 25° was added 20.7 g of activated manganese oxide and the mixture was stirred for 2 hours. After filtration, the filtrate was concentrated in vacuo to yield 1.50 g (73% yield) of the titled compound.

Anaylsis Calculated for $C_{17}H_{20}O_4$: C, 70.81; H, 6.99. Found: C, 70.96; H, 6.87.

EXAMPLE 62

Preparation of 6-(4-Acetyl-3-hydroxy-2-propylphenoxy)-2-hexynoic acid

To 0.58 g of chromium triqxide in 8 ml of 10N sulfuric acid cooled at 0° was added a solution of 1.51 g of 6-(4-acetyl-3-hydroxy-2-propylphenoxy)-2-hexynal in 15 ml of acetone over 30 minutes with stirring. The reaction mixture was allowed to warm to 25° over 30 minutes and then concentrated in vacuo to remove the acetone. Water (50 ml) was added and the product was extracted with ether. The ether phase was extracted with 1.0N sodium hydroxide, the aqueous layer was separated, acidified and extracted with ether. The dried (over sodium sulfate) extract was concentrated in vacuo to a solid which was crystallized twice from ether-hexane to give 0.63 g, mp 115–116°, (40% yield) of 6-(4-acetyl-3-hydroxy-2-propylphenoxy)-2-hexynoic acid, the titled compound.

EXAMPLE 63

Preparation of 6-(4-Acetyl-3-hydroxy-2-propylphenoxy)-1-chloro-4-hexyne

A mixture of 3.10 g of 1-(2,4-dihydroxy-3-propylphenyl) ethanone, 3.13 g of 1-bromo-6-chloro-2-hexyne and 3.30 g of anhydrous potassium carbonate in 35 ml of anhydrous acetone was stirred at reflux for 2.5 hours. The solvent was removed in vacuo, water was added to the residue and the pH was adjusted to 4.0. The product was extracted with ether and the dried (over magnesium sulfate) extract was chromatographed on 250 g of silica gel. Elution with 25% ethyl acetate-hexane gave 4.30 g (88% yield) of 6-(4-acetyl- 3-hydroxy-2-propylphenoxy)-1-chloro-4-hexyne, the titled compound.

EXAMPLE 64

Preparation of 7-(4-Acetyl-3-hydroxy-2-propylphenoxy)-5-hexynenitrile

A solution of 3.98 g of 6-(4-acetyl-3-hydroxy-2-propylphenoxy)-1-chloro-4-hexyne, 0.95 g of sodium cyanide and 1.90 g of sodium iodide in 125 ml of anhydrous dimethylformamide was stirred and heated at 80° for 3 hr. The solvent was removed in vacuo, water was added to the residue and the product was extracted with ether. The dried (over magnesium sulfate) extract was chromatographed on 250 g of silica gel and eluted with 20% ethyl acetate-hexane to give 2.73 g (71% yield) of 7-(4-acetyl-3-hydroxy-2-propylphenoxy)-5-hexynenitrile, the titled compound as an oil.

Analysis Calculated for $C_{18}H_{21}NO_3$: C, 72.22; H, 7.07; N, 4.68. Found: C, 71.94; H, 6.98; N, 4.76.

EXAMPLE 65

Preparation of 6-(4-Acetyl-3-hydroxy-2-propylphenoxy)-5-heptynoic acid

A solution of 2.36 g of 7-(4-acetyl-3-hydroxy-2-propylphenoxy)-5-hexynenitrile and 47 ml of 5.0N sodium hydroxide in 95 ml of ethylene glycol was stirred and heated at 140° for 1 hour. After cooling, 300 ml of water was added, the pH was ajusted to 2.0 and the product was extracted with ether. The extract was washed twice with water, dried (MgSO4) and concentrated in vacuo to a solid which was crystallized fom ether-hexane to yield 2.03 g, mp 84–86°, (81% yield) of 6-(4-acetyl-3-hydroxy-2-propylphenoxy)-5-heptynoic acid, the title compound.

Analysis Calculated for $C_{18}H_{22}O_5$: C, 67.91; H, 6.97. Found: C, 67.92; H, 6.88.

EXAMPLE 66

Preparation of 3-[2-(4-Acetyl-3-hydroxy-2-propylphenoxy) ethoxy]propanoic acid semihydrate A mixture of 1.94 g of 1-(2,4-dihydroxy-3-propylphenyl) ethanone, 7.00 g of bis-2-bromoethyl ether and 1.70 g of anhydrous potassium carbonate in 25 ml of anhydrous acetone was stirred at reflux for 20 hours. The reaction mixture was filtered and the filtrate was concentrated in vacuo to an oil which was chromatographed on 250 g of silica gel. Elution with 5% ethyl acetate-toluene gave 2.66 g (77% yield) of 1-[4-[2-(2-bromoethoxy)ethoxy]-2-hydroxy-3-propyl phenyl]ethanone as an oil. The low resolution mass spectrum gave the molecular ion peak at m/e 344.

A solution of 2.60 g of 1-[4-[2-(2-bromoethoxy)ethoxy]-2-hydroxy-3-propylphenyl]ethanone, 0.50 g of sodium cyanide and 1.13 g of sodium iodide in 50 ml of dimethyl formamide was stirred and heated at 80° for 6 hours. The solvent was removed in vacuo, water was added to the residue and the product was extracted with ether. The dried (over magnesium sulfate) extract was concentrated in vacuo to give 2.13 g of impure 3-[2-(4-acetyl-3-hydroxy-2-propylphenoxy)ethoxy]propanenitrile.

A solution of 1.96 g of crude 3-[2-(4-acetyl-3-hydroxy-2-propylphenoxy)ethoxy]propanenitrile in 40 ml of ether and 40 ml of methanol was cooled in an ice bath while hydrogen chloride gas was bubbled through the solution for 10 minutes. The solution was cooled in the ice bath for 1 hour and then left at 23° for 16 hours. Nitrogen was bubbled through the solution to remove some of the excess hydrochloric acid and then 20 ml of water was added. Saturated sodium bicarbonate solution was added to neutralize the hydrochloric acid and the ether layer was separated. The aqueous layer was extracted with ethyl acetate and the combined extract was washed with sodium bicarbonate solution, dried (over magnesium sulfate) and concentrated in vacuo to an oil. Chromatography on 170 g of silica gel and elution with 30% ethyl acetate-toluene gave 1.01 g of crude 3-[2-(4-acetyl-3-hydroxy-2-propylphenoxy) ethoxy]propanoic acid methyl ester. The low resolution mass spectrum showed the molecular ion at m/e 324.

A solution of 1.01 g of crude 3-[2-(4-acetyl-3-hydroxy-2- propylphenoxy)ethoxy]propanoic acid methyl ester in 15 ml of methanol and 15 ml of 1.0 N sodium hydroxide was stirred at 23° for 7 hours. The methanol was removed in vacuo, the residue was acidified and the product was extracted with ethyl acetate. The dried (over magnesium sulfate) extract was concentrated in vacuo to a solid which was recrystallized from ether-hexane to give 0.71 g, mp 48–50°, of 3-[2-(4-acetyl-3-hydroxy-2-propylphenoxy)ethoxy]propanoic acid semihydrate.

Analysis Calculated for $C_{16}H_{22}O_6 \cdot 0.5\ H_2O$: C, 60.17; H, 7.26; $H_2O$, 2.82. Found: C, 60.07; H, 7.42; $H_2O$, 2.53.

EXAMPLE 67

3-[2-[2-[2-(4-Acetyl-3-hydroxy-2-propylphenoxy)ethoxy]ethoxy]ethoxy]propanoic acid semihydrate.

A mixture of 1.94 g of 1-(2,4-dihydroxy-3-propylphenyl, ethanone, 10 g of 1,11-dibromo-3,6,9-trioxaundecane and 1.7 g of anhydrous potassium carbonate in 25 ml of anhydrous acetone was stirred at reflux for 20 hours. The reaction mixture was filtered and the filtrate was concentrated in vacuo to an oil which was purified by high pressure liquid chromatography using 25% ethyl acetate-hexane to give 2.23 g (52% yield) of 1-[4-[2-[2-[2-(2-bromoethoxy)ethoxy]ethoxy]ethoxy]-2-hydroxy-3-propylphenyl]ethanone. The low resolution mass spectrum showed the molecular ion peak at m/e 432.

A solution of 2.23 g of 1-[4-[2-[2-[2-(2-bromoethoxy)ethoxy]ethoxy]-2-hydroxy-3-propylphenyl]ethanone, 0.34 g of sodium cyanide and 0.77 g of sodium iodide in 40 ml of dimethyl formamide was stirred and heated at 80° for 70 minutes. The solvent was removed in vacuo, water was added to the residue and the product was extracted with ether. The dried (over magnesium sulfate) extract was concentrated in vacuo to give 1.93 g of crude 3-[2-[2-[2- (4-acetyl-3-hydroxy-2-propylphenoxy)ethoxy]ethoxy]ethoxy] propanenitrile. The low resolution mass spectrum showed the molecular ion at m/e 379.

A solution of 1.93 g of crude 3-[2-[2-[2-(4-acetyl-3-hydroxy-2-propylphenoxy)ethoxy]ethoxy]ethoxy]-propanenitrile in 40 ml of ether and 40 ml of methanol was cooled in an ice bath while hydrogen chloride was bubbled through the solution for 10 minutes. The solution was kept in the ice bath for 1.5 hours and at 23° for 2 hours. Nitrogen was bubbled through to remove some of the excess hydrochloric acid and then 20 ml of water was added. Solid sodium bicarbonate was added to neutralize the hydrochloric acid and the product was extracted with ethyl acetate after saturating the aqueous layer with sodium chloride. The dried (over magnesium sulfate) extract was concentrated in vacuo to yield 1.91 g of crude 3-[2-[2-[2-(4-acetyl-3-hydroxy-2-propylphenoxy)ethoxy]ethoxy]ethoxy]propanoic acid methyl ester.

A solution of 1.91 g of 3-[2-[2-[2-(4-acetyl-3-hydroxy-2-propylphenoxy)ethoxy]ethoxy]ethoxy]propanoic acid methyl ester in 30 ml of methanol and 23 ml of 1.0 N sodium hydroxide was stirred at 23° for 17 hours. The methanol was removed in vacuo, the residue was acidified and the product was extracted with ethyl acetate. The dried (over magnesium sulfate) extract was concentrated in vacuo to an oil (1.60 g) which was chromatographed on 170 g of silica gel. Elution with 10% acetic acid:25% ethyl acetate:65% toluene gave 1.28 g of 3-[2-[2-[2-(4-acetyl-3-hydroxy-2-propylphenoxy)ethoxy]ethoxy]ethoxy]propanoic acid semihydrate.

Analysis Calculated for $C_{20}H_{38}O_8 \cdot 0.5 H_2O$: C, 58.95; H, 7.67; $H_2O$, 2.21. Found: C, 59.61; H, 7.63; $H_2O$, 2.16.

EXAMPLE 68

Preparation of 7-(4-Acetyl-3-hydroxy-2-propylphenoxy) heptanoic acid.

A mixture of 5.8 g of 1-(2,4-dihydroxy-3-propylphenyl) ethanone, 5.4 ml of 7-bromoheptanenitrile and 8.3 g of anhydrous potassium carbonate in 50 ml of dimethyl formamide was stirred and heated at 75° for 20 hours. The reaction mixture was filtered and the filtrate was concentrated on the oil pump. The residual oil was chromatographed on 200 g of silica gel using 5% ethyl acetate-toluene to give 7.5 g (83% yield) of 7-(4-acetyl-3-hydroxy-2-propylphenoxy)heptane nitrile. This was dissolved in 200 ml of ether-methanol (1:1) and cooled in an ice bath while a stream of hydrochloric acid gas was introduced for 10 minutes. The reaction mixture was kept at 3° for 1 hour and at room temperature for 16 hours. Water (40 ml) was added and most of the solvent was removed in vacuo. The residue was treated with sodium bicarbonate solution to basify and the product was extracted with ether. The crude product was dissolved in 140 ml of methanol, treated with 120 ml of 1N sodium hydroxide and the solution was heated on the stream bath for 10 minutes and left at room temperature for 66 hours. The methanol was removed in vacuo and the aqueous solution was extracted with ether. The basic aqueous layer was acidified and extracted with ether. The dried (over magnesium sulfate) extract was concentrated and chromatographed on 50 g of silica gel. Elution with acetic acid (5): ethyl acetate (25): toluene (70) and crystallization of the combined pure fractions from ether-hexane gave 2.20 g, mp 64–66°, of 7-(4-acetyl-3-hydroxy-2-propylphenoxy)heptanoic acid.

Analysis Calculated for $C_{18}H_{26}O_5$: C, 67.06; H, 8.13. Found C, 67.08; H, 7.97.

EXAMPLE 69

Preparation of 4-[(4-Acetyl-3-hydroxy-2-propylphenoxy) methyl]benzoic acid methyl ester A mixture of 2.50 g of 1-(2,4-hydroxy-3-propylphenyl)ethenone, 2.95 g of methyl 4-bromomethylbenzoate and 2.70 g of anhydrous potassium carbonate in 50 mL of anhydrous acetone was stirred at reflux for 2.5 hours. The reaction mixture was filtered and the filtrate was concentrated in vacuo to a solid. Recrystallization from hexane gave 3.35 g, mp 98°–100°, (76% yield) of 4-[(4-acetyl-3-hydroxy-2-proplyphenoxy)methyl]benzoic acid methyl ester, the title compound.

Analysis Calculated for $C_{20}H_{22}O_5$: C, 70.16; H, 6.48. Found: C, 70.10; H, 6.49.

EXAMPLE 70

Preparation of 4-[(4-Acetyl-3-hydroxy-2-propylphenoxy) methyl]benzoic acid

A solution of 3.30 g 4-[(4-acetyl-3-hydroxy-2-propylphenoxy)methyl]benzoic acid methyl ester and 48 mL of 1.0 N sodium hydroxide dissolved in 100 mL of methanol was stirred at reflux for 1.25 hour. The solvent was removed in vacuo and the reaction mixture was acidified with 6 N hydrochloric acid. The product was extracted with ethyl acetate and the dried (over magnesium sulfate) extract was concentrated in vacuo to give a solid. Recrystallization from acetonehexane gave 2.613 g, mg 187°–189°, (83% yield) of 4-[(4-acetyl-3-hydroxy-2-propylphenoxy)methyl]benzoic acid, the title compound.

The analytical sample was recrystallized from methylene chloride-ether mp 188°–189°.

Analysis Calculated for $C_{19}H_{20}O_5$: C, 69.50; H, 6.14. Found: C, 69.30; H, 6.36.

EXAMPLE 71

Preparation of
3-[(4-Acetyl-3-hydroxy-2-propylphenoxy)
methyl]benzoic acid methyl ester 1-(2,4-dihydroxy-3-propylphenyl)ethanone was allowed to react with methyl 3-bromomethylbenzoate according to the procedure of Example 69 and the product was purified by recrystallization from methylene chloride-ether to give 3-[(4-acetyl-3-hydroxy-2-propylphenoxy)methyl]benzoic acid methyl ester, the title compound, mp 141°–143°, in 89% yield. Analysis Calculated for $C_{20}H_{22}O_5$: C, 70.16; H, 6.48. Found: C, 69.99; H, 6.41.

EXAMPLE 72

Preparation of
3-[(4-Acetyl-3-hydroxy-2-propylphenoxy)
methyl]benzoic acid

3-[(4-Acetyl-3-hydroxy-2-propylphenoxy)methyl]-benzoic acid methyl ester was allowed to react with 1.0N sodium hydroxide according to the procedure of Example 70 and the product was purified by recrystallization from acetone to give 3-[(4-acetyl-3-hydroxy-2-propylphenoxy)methyl]benzoic acid, the title compound, m.p. 221°–224°, in 92% yield. Analysis Calculated for $C_{19}H_{20}O_5$: C, 69.50; H, 6.14. Found: C, 69.64; H, 6.35.

EXAMPLE 73

Preparation of
2-[(4-Acetyl-3-hydroxy-2-propylphenoxy)
methyl]benzoic acid methyl ester 1-(2,4-dihydroxy-3-propylphenyl)ethanone was allowed to react with methyl 2-bromomethylbenzoate according to the procedure of Example 69 and the product was purified by recrystallization from hexane to give 2-[4-acetyl-3-hydroxy-2-propylphenoxy)methyl]benzoic acid methyl ester, the title compound, m.p. 90°–93°, in 78% yield. Analysis Calculated for $C_{20}H_{22}O_5$: C, 70.16, H, 6.48. Found: C, 69.97; H, 6.36.

EXAMPLE 74

Preparation of
2-[(4-Acetyl-3-hydroxy-2-propylphenoxy)
methyl]benzoic acid

2-[(4-Acetyl-3-hydroxy-2-propylphenoxy)methyl]-benzoic acid methyl ester was allowed to react with 1.0N sodium hydroxide according to the procedure of Example 70 and the product was purified by recrystallization from methanol to give 2-[(4-acetyl-3-hydroxy-2-propylphenoxy)methyl]benzoic acid, the title compound, m.p. 216°–219°, in 85% yield. Analysis Calculated for $C_{19}H_{20}O_5$: C, 69.50; H, 6.14. Found: C, 69.39; H, 6.19.

EXAMPLE 75

Preparation of
3-[(4-Acetyl-3-hydroxy-2-propylphenoxy)
methyl]-2-ethoxybenzoic acid ethyl ester 1-(2,4-dihydroxy-3-propylphenyl)ethanone was allowed to react with 3-(bromomethyl)-2-ethoxybenzoic acid ethyl ester according to the procedure of Example 69 and the product was purified by HPLC to give 3--[(4-acetyl-3-hydroxy-2-propylphenoxy)methyl]-2-ethoxybenzoic acid ethyl ester, the title compound, m.p. 59°–62° in 90% yield.

Analysis Calculated for $C_{23}H_{28}O_6$: C, 68.69; H, 77.05. Found: C, 68.87; H, 6.88.

EXAMPLE 76

Preparation of
3-[(4-Acetyl-3-hydroxy-2-propylphenoxy)
methyl]-2-ethoxybenzoic acid 3[(4-Acetyl-3-hydroxy-2-propylphenoxy)methyl]-2-ethoxybenzoic acid ethyl ester was allowed to react with 1.0N sodium hydroxide according to the procedure of Example 70 and the product was purified by recrystallization from methanol to give 3-[(4-acetyl-3-hydroxy-2-propylphenoxy)methyl]-2- ethoxybenzoic acid, the title compound, m.p. 154°–156° in 85% yield.

Analysis Calculated for $C_{21}H_{24}O_6$: C, 67.73; H, 6.50. Found: C, 67.76; H, 6.46.

EXAMPLE 77

Preparation of
4-[(4-Acetyl-3-hydroxy-2-propylphenoxy)
methyl]-2-ethoxybenzoic acid ethyl ester 1-(2,4-dihydroxy-3-propylphenyl)ethanone was allowed to react with 4-(bromomethyl)-2-ethoxybenzoic acid ethyl ester according to the procedure of Example 69 and the product was purified by HPLC to give 4-[(4-acetyl-3-hydroxy-2-propylphenoxy)methyl]-2-ethoxybenzoic acid ethyl ester, the title compound, m.p. 92°–94° in 83% yield.

Analysis Calculated for $C_{23}H_{28}O_6$: C, 68.98; H, 7.05. Found: C, 68.87; H, 6.96.

EXAMPLE 78

Preparation of
4[(4-Acetyl-3-hydroxy-2-propylphenoxy)
methyl]-2-ethoxybenzoic acid 4-[(4-Acetyl-3-hydroxy-2-propylphenoxy)methyl]-2-ethoxybenzoic acid ethyl ester was allowed to react with 1.0N sodium hydroxide according to the procedure of Example 70 and the product was purified by recrystallization from methanol to give 4[(4-acetyl-3-hydroxy-2-propylphenoxy) methyl]-2-ethoxybenzoic acid, the title compound, m.p. 145°–150° in 93% yield.

Analysis Calculated for $C_{21}H_{24}O_6$: C, 67.73; H, 6.50. Found: C, 67.51; H, 6.59.

EXAMPLE 79

Preparation of
4-[2-(4-Acetyl-3-hydroxy-2-propylphenoxy)
ethoxy]benzoic acid ethyl ester A mixture of 1.5 g of 1-[4-(2-bromoethoxy)-2-hydroxy-3- propylphenyl]ethanone 0.83 g of 4-hydroxybenzoic acid ethyl ester and 0.95 g of anhydrous potassium carbonate in 30 ml of anhydrous acetone and 10 ml of anhydrous DMF was stirred at reflux for 20 hours. The mixture was filtered and solvent was removed in vacuo. The residue was dissolved in ethyl acetic and washed with water. The extract was dried over magnesium sulfate) and concentrated in vacuo to an oil which was purified by HPLC using 25% ethyl acetate-hexane to give 1.3 g, m.p. 99–100 (75%) of 4-[2-(4-acetyl-3-hydroxy-2-propylphenoxy)ethoxy]-benzoic acid ethyl ester, the title compound. Analysis Calculated for $C_{22}H_{26}O_6$: C, 68.36; H, 6.78. Found: C, 68.39; H, 6.79.

EXAMPLE 80

Preparation of 4-[2-(4-Acetyl-3-hydroxy-2-propylphenoxy)ethoxy]-benzoic acid

A solution of 1.44 g of 4-[2-(4-acetyl-3-hydroxy-2-propylphenoxy)ethoxy]-benzoic acid ethyl ester in 18 ml of methanol and 18ml of 1N sodium hydroxide was stirred at reflux for 25 minutes. The methanol was removed in vacuo and the aqueous solution was diluted with water. The pH of solution was adjusted to 2.0 with 3N hydrochloric acid. The precipitate was extracted with methanol. The extract was washed with water, dried (over magnesium sulfate) and concentrated in vacuo to a solid which was treated with ether filtered to give 1.2 g , m.p. 175–176° (90%) of 4-[2-(4-acetyl-3-hydroxy-2-propylphenoxy)ethoxy]-benzoic acid, the title compound.

EXAMPLE 81

Preparation of 3-[2-(4-Acetyl-3-hydroxy-2-propylphenoxy)ethoxy]benzoic acid ethyl ester A mixture of 1.5 g of 1-[4-(2-bromoethoxy)-3-hydroxy-2-propylphenyl]ethanone, 0.83 g of ethyl 3-hydroxybenzoate and 0.95 g of potassium carbonate was allowed to react according to the procedure of Example 79 to give 1.2 g, m.p. 58–60° (62% yield) of 3-[2-(4-acetyl-3-hydroxy-2-propylphenoxy)ethoxy]benzoic acid ethyl ester, the title compound.

Analysis Calculated for $C_{22}H_{26}O_6$: C, 68.36; H, 6.78. Found: C, 68.54; H, 6.78.

EXAMPLE 82

Preparation of 3-[2-(4-Acetyl-3-hydroxy-2-propylphenoxy)ethoxy]-benzoic acid

Hydrolysis of 1.2 g of 3-[2-(4-acetyl-3-hydroxy-2-propylphenoxy)ethoxy]benzoic acid ethyl ester by the procedure in Example 80 gave 1.1 g, m.p. 155°, (99% yield) of 3-[2-(4-acetyl-3-hydroxy-2-propylphenoxy)ethoxy]benzoic acid, the title compound.

Analysis Calculated for $C_{20}H_{22}O_6$: C, 67.03; H, 6.19. Found: C, 66.86; H, 6.15.

EXAMPLE 83

Preparation of 2-[2-(4-Acetyl-3-hydroxy-2-propylphenoxy)ethoxy]-benzoic acid methyl ester A mixture of 1.5 g of 1-[4-(2-bromoethoxy)-3-hydroxy-2-propylphenyl]ethanone, 0.76 g of ethyl 2-hydroxybenzoate and 1.05 g of potassium carbonate was allowed to react according to the procedure of Example 79 to give 1.1 g, m.p. 84°–87°, (59% yield) of 2-[2-(4-acetyl-3-hydroxy-2-propylphenoxy)ethoxy]benzoic acid methyl ester, the title compound.

Analysis Calculated for $C_{22}H_{26}O_6$: C, 68.36; H, 6.78. Found: C, 67.81; H, 6.67.

EXAMPLE 84

Preparation of 2-[2-(4-Acetyl-3-hydroxy-2-propylphenoxy)ethoxy]-benzoic acid

Hydrolysis of 1.1 g of 2-[2-(4-acetyl-3-hydroxy-2-propylphenoxy)ethoxy]benzoic acid methyl ester by the procedure in Example 80 gave 0.85 g, m.p. 108°–110°, (79% yield) of 2-[2-(4-Acetyl-3-hydroxy-2-propylphenoxy)ethoxy]benzoic acid, the title compound.

Analysis Calculated for $C_{20}H_{22}O_6$: C, 67.03; H, 6.19. Found: C, 66.79; H, 6.15.

EXAMPLE 85

Preparation of 4-[3-(4-Acetyl-3-hydroxy-2-propylphenoxy)propoxy]-benzoic acid ethyl ester A mixture of 2.00 g of 1-[4-(3-bromopropoxy)-3-hydroxy-2-propylphenoxy]ethanone, 1.05 g of ethyl 4-hydroxybenzoate and 1.30 g of potassium carbonate was allowed to react according to Example 79 to give 2.21 g, m.p. 86°–87°, (87% yield) of 4-[3-(4-acetyl-3-hydroxy-2-propylphenoxy)propoxy]benzoic acid ethyl ester, the title compound.

Analysis Calculated for $C_{23}H_{28}O_6$: C, 68.98; H, 7.05. Found: C, 68.80; H, 6.92.

EXAMPLE 86

Preparation of 4-[3-(4-Acetyl-3-hydroxy-2-propylphenoxy)propoxy]-benzoic acid

Hydrolysis of 2.11 g of 4-[3-(4-acetyl-3-hydroxy-2-propylphenoxy)propoxy]benzoic acid ethyl ester by the procedure in Example 80 gave 1.80 g, m.p. 180°–183°; (92% yield) of 4-[3-(4-acetyl-3-hydroxy-2-propylphenoxy)propoxy]benzoic acid, the title compound.

Analysis Calculated for $C_{21}H_{24}O_6$: C, 67.73; H, 6.50. Found: C, 67.41; H, 6.47.

EXAMPLE 87

Preparation of 3-[3-(4-Acetyl-3-hydroxy-2-propylphenoxy)propoxy]-benzoic acid ethyl ester A mixture of 1.5 g of 1-[4-(3-bromopropoxy)-3-hydroxy-2-propylphenyl]ethanone, 0.79 g of ethyl 3-hydroxybenzoate and 1.0 g of potassium carbonate was allowed to react according to Example 79 to give 1.6 g (83% yield) of 3-[3-(4-Acetyl-3-hydroxy-2-propylphenoxy)propoxy]benzoic acid ethyl ester, the title compound as an oil.

Analysis Calculated for $C_{23}H_{28}O_6$: C, 68.98; H, 7.05. Found: C, 68.76; H, 77.01.

EXAMPLE 88

Preparation of 3-[3-(4-Acetyl-3-hydroxy-2-propylphenoxy)propoxy]-benzoic acid

Hydrolysis of 1.4 g of 3-[3-(4-acetyl-3-hydroxy-2-propylphenoxy)propoxy]benzoic acid ethyl ester by the procedure in Example 80 gave 1.0 g, m.p. 142°–143°, (77% yield) of 3-[3-(4-Acetyl-3-hydroxy-2-propylphenoxy)propoxy]benzoic acid, the title compound.

Analysis Calculated for $C_{21}H_{24}O_6$: C, 67.73; H, 6.50. Found: C, 67.95; H, 6.74.

EXAMPLE 89

Preparation of 2-[3-(4-Acetyl-3-hydroxy-2-propylphenoxy)propoxy]-benzoic acid methyl ester A mixture of 1.5 g of 1-[4-(3-bromopropoxy)-3-hydroxy-2-propylphenyl]ethanone, 0.73 g of methyl 2-hydroxybenzoate and 1.0 g of potassium carbonate was allowed to react according to Example 79 to give 1.15 g (62% yield) of 2-[3-(4-acetyl-3-hydroxy-2- propylphenoxy)propoxy]benzoic acid methyl ester, the title compound as an oil.

Analysis Calculated for $C_{23}H_{28}O_6$: C, 68.98; H, 7.05. Found: C, 68.48; H, 6.77.

EXAMPLE 90

Preparation of 2-[3-(4-Acetyl-3-hydroxy-2-propylphenoxy)propoxy]-benzoic acid

Hydrolysis of 1.15 g of 2-[3-(4-acetyl-3-hydroxy-2-propylphenoxy)propoxy]benzoic acid methyl ester by the procedure in Example 80 gave 0.79 g, m.p. 105°–108°, (71% yield) of 2-[3-(4-acetyl-3-hydroxy-2-propylphenoxy)propoxy]benzoic acid, the title compound.

Analysis Calculated for $C_{21}H_{24}O_6$: C, 67.73; H, 6.50. Found: C, 67.77; H, 6.76.

EXAMPLE 91

TABLET FORMULATION
(Wet granulation)

| Item | Ingredient | mg/ tablet | mg/ tablet | mg/ tablet |
|---|---|---|---|---|
| 1. | 6-(4-acetyl-3-hydroxy-2-propylphenoxy)-N—[4-(3-pyridinyl)butyl]hexanamide hydrochloride | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
|  | Weight of tablet | 245 mg | 490 mg | 795 mg |

Procedure:
(1) Mix items 1, 2, 4 and 5 in a suitable mixer, granulate with polyvinyl pyrrolidone and dissolve in water/alcohol. Dry the granulation. Mill the dry granulation through a suitable mill.
(2) Add magnesium stearate and compress on a suitable press.

EXAMPLE 92

TABLET FORMULATION
(Wet granulation)

| Item | Ingredient | mg/ tablet | mg/ tablet | mg/ tablet |
|---|---|---|---|---|
| 1. | 6-(4-acetyl-3-hydroxy-2-propylphenoxy)-N—[4-(3-pyridinyl)butyl]hexanamide hydrochloride | 100 | 250 | 500 |
| 2. | Lactose | 147.5 | 100 | 97.5 |
| 3. | Pregelatinized starch | 25 | 30 | 60 |
| 4. | Modified starch | 25 | 50 | 60 |
| 5. | Corn starch | 25 | 50 | 60 |
| 6. | Magnesium stearate | 2.5 | 5 | 7.5 |
|  | Weight of tablet | 325 mg | 500 mg | 785 mg |

Procedure:
(1) Mix items 1, 2, 3, 4 and 5 in a suitable mixer, granulate with water, and dry over night in a suitable oven. Mill through suitable mill.
(2) Mix with item 6 and compress on a suitable press.

EXAMPLE 93

CAPSULE FORMULATION

| Item | Ingredient | mg/ capsule | mg/ capsule | mg/ capsule |
|---|---|---|---|---|
| 1. | 6-(4-acetyl-3-hydroxy-2-propylphenoxy)-N—[4-(3-pyridinyl)butyl]hexanamide hydrochloride | 100 | 250 | 500 |
| 2. | Lactose | 99 | 148 | — |

-continued

CAPSULE FORMULATION

| Item | Ingredient | mg/ capsule | mg/ capsule | mg/ capsule |
|---|---|---|---|---|
| 3. | Corn starch | 20 | 30 | 57 |
| 4. | Talc | 5 | 10 | 15 |
| 5. | Magnesium stearate | 1 | 2 | 3 |
|  | Fill weight of capsule | 225 mg | 440 mg | 575 mg |

Procedure:
(1) Mix items 1, 2, and 3 in a suitable mixer. Mill through suitable mill.
(2) Mix the mixture in Step 1 with items 4 and 5 and fill on a suitable machine.

We claim:
1. A compound of the formula

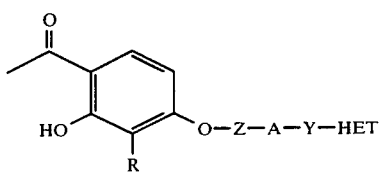

wherein R is hydrogen or lower alkyl; Y is alkylene; Z is alkylene,

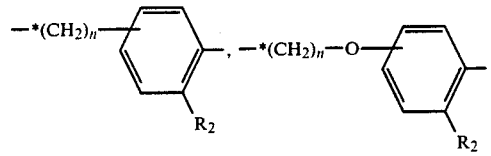

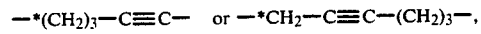

the asterisk herein denotes bonding to the substituted acetophenone; $R_2$ is hydrogen or lower alkoxy; n is an integer of 1 to 3; A is

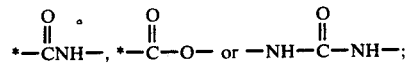

and HET is a 5- or 6-membered nitrogen containing heterocyclic group selected from the group consisting of 3-pyridinyl, 4-pyridinyl, 3-pyridinyloxy, 3-pyridinylthio, 5-pyrimidinyl and 1H-imidazol-1-yl.

2. A compound, in accordance with claim 1, wherein R is lower alkyl.

3. A compound, in accordance with claim 2, wherein the heterocyclic group is 3-pyridinyl.

4. A compound, in accordance with claim 3, wherein Z is alkylene.

5. A compound, in accordance with claim 3, wherein Z is *—$(CH_2)_3$C≡C—.

6. A compound, in accordance with claim 4, wherein A is

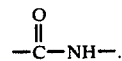

7. A compound, in accordance with claim 4, wherein A is

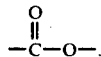

8. A compound, in accordance with claim 4, wherein A is

9. A compound, in accordance with claim 1, 5-(4-acetyl-3-hydroxy-2-propylphenoxy)-N-[4-(3-pyridinyl)butyl]pentanamide.

10. A compound, in accordance with claim 1, 6-(4-acetyl-3-hydroxy-2-propylphenoxy)-N-[4-(3-pyridinyl)butyl]hexanamide.

11. A compound, in accordance with claim 1, 4-(4-acetyl-3-hydroxy-2-propylphenoxy)-N-[4(3-pyridinyl)butyl]butanamide.

12. A compound in accordance with claim 1, 6-(4-acetyl-3-hydroxy-2-propylphenoxy)-N-[4-(5-pyrimidinyl)butyl]hexanamide.

13. A compound, in accordance with claim 1, 7-(4-acetyl-3-hydroxy-2propylphenoxy)-N-[4(3-pyridinyl)butyl]-5-heptynamide.

14. A compound, in accordance with claim 1, N-[5-(4-acetyl-3-hydroxy-2-propylphenoxy)pentyl]-N'-[4-(3-pyridinyl)butyl]urea.

15. A compound, in accordance with claim 1, 3-(4-acetyl-3-hydroxy-2-propylphenoxy)propyl-N'-[4-(3-pyridinyl)butyl]benzamide.

16. A pharmaceutical composition comprising an effective amount of the formula

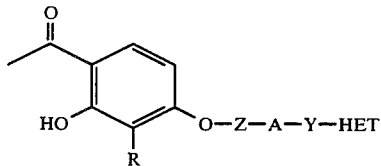           I wherein R is hydrogen or lower alkyl; Y is alkylene; Z is alkylene,

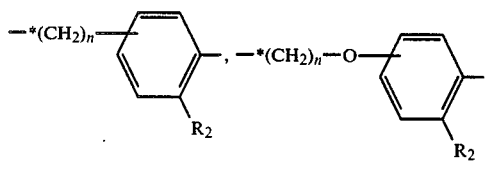

—*(CH₂)₃—C≡C—  or  —*CH₂—C≡C—(CH₂)₃—, the asterisk herein denotes bonding to the substituted acetophenone; R₂ is hydrogen or lower alkoxy; n is an integer of 1 to 3; A is

and HET is a 5- or 6-membered nitrogen containing heterocyclic group selected from the group consisting of 3-pyridinyl, 4-pyridinyl, 3-pyridinyloxy, 3-pyridinylthio, 5-pyrimidinyl and 1H-imidazol-1-yl.

17. A pharmaceutical composition, in accordance with claim 16, wherein R is lower alkyl.

18. A pharmaceutical composition, in accordance with claim 17, wherein the heterocyclic group is 3-pyridinyl.

19. A pharmaceutical composition, in accordance with claim 18, wherein Z is alkylene.

20. A pharmaceutical composition, in accordance with claim 19, wherein A is

21. A pharmaceutical composition in accordance with claim 19, wherein A is -

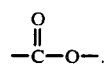

22. A pharmaceutical composition, in accordance with claim 19, wherein A is

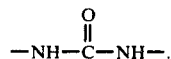

23. A pharmaceutical composition, in accordance with claim 16, wherein the compound of formula I is 5-(4-acetyl-3-hydroxy-2-propylphenoxy)-N-[4-(3-pyridinyl)butyl]pentanamide.

24. A pharmaceutical composition, in accordance with claim 16, wherein the compound of formula I is 6-(4-acetyl-3-hydroxy-2-propylphenoxy)-N-[4(3-pyridinyl)butyl]hexanamide.

25. A pharmaceutical composition, in accordance with claim 16, wherein the compound of formula I is 4-(4-acetyl-3-hydroxy-2-propylphenoxy)-N-[4-(3-pyridinyl)butyl]butanamide.

26. A pharmaceutical composition, in accordance with claim 16, wherein the compound of formula I is 6-(4-acetyl-3-hydroxy-2-propylphenoxy)-N-[4-(5-pyrimidinyl)butyl]hexanamide.

27. A pharmaceutical composition, in accordance with claim 16, wherein the compound of formula I is 7-(4-acetyl-3-hydroxy-2-propylphenoxy)-N-[4-(3-pyridinyl)butyl]-5-heptynamide.

28. A pharmaceutical composition, in accordance with claim 16, wherein the compound of formula I is N-[5-(4-acetyl-3-hydroxy-2-propylphenoxy)pentyl]-N'-[4-(3-pyridinyl)butyl]urea.

29. A pharmaceutical composition, in accordance with claim 16, wherein the compound of formula I is 3-(4-acetyl-3-hydroxy-2-propylphenoxy)methyl-N-[4-(3-pyridinyl)butyl]benzamide.

30. A method of treating allergic conditions in which slow reacting substance of anaphylaxis is a mediator which comprises administering an effective amount of a compound of formula I

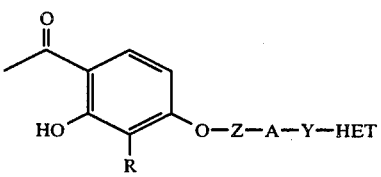           I wherein R is hydrogen or lower alkyl; Y ia alkylene; Z is alkylene,

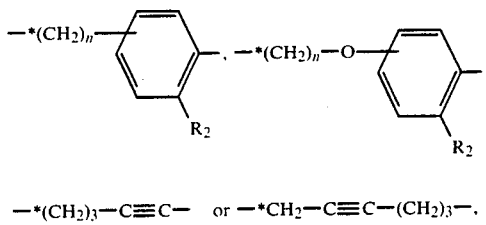

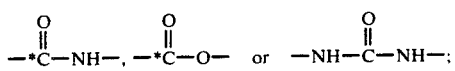

the asterisk herein denotes bonding to the substituted acetophenone; R₂ is hydrogen or lower alkoxy; n is an integer of 1 to 3; A is

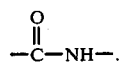

and HET is a 5- or 6-membered nitrogen containing heterocyclic group selected from the group consisting of 3-pyridinyl, 4-pyridinyl, 3-pyridinyloxy, 3-pyridinylthio, 5-pyrimidinyl and 1H-imidazol-1-yl.

31. A method, in accordance with claim 30, wherein R is lower alkyl.

32. A method, in accordance with claim 31, wherein the heterocyclic group is 3-pyridinyl.

33. A method, in accordance with claim 32, wherein Z is alkylene.

34. A method, in accordance with claim 33, wherein A is

—C(=O)—NH—.

35. A method, in accordance with claim 33, wherein A is

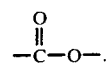

36. A method, in accordance with claim 33, wherein A is

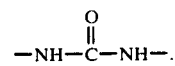

37. A method, in accordance with claim 30, wherein the compound of formula I is 5-(4-acetyl-3-hydroxy-2-propylphenoxy)-N-[4-(3-pyridinyl)butyl]pentanamide.

38. A method, in accordance with claim 30, wherein the compound of formula I is 6-(4-acetyl-3-hydroxy-2-propylphenoxy)-N-[4-(3-pyridinyl)butyl]hexanamide.

39. A method, in accordance with claim 30, wherein the compound of formula I is 4-(4-acetyl-3-hydroxy-2-propylphenoxy)-N-[4-(3-pyridinyl)butyl]butanamide.

40. A method, in accordance with claim 30, wherein the compound of formula I is 6-(4-acetyl-3-hydroxy-2-propylphenoxy)-N-[4-(5-pyrimidinyl)butyl]hexanamide.

41. A method, in accordance with claim 30, wherein the compound of formula I is 7-(4-acetyl-3-hydroxy-2-propylphenoxy)-N-[4-(3-pyridinyl)butyl]-5-heptynamide.

42. A method, in accordance with claim 30, wherein the compound of formula I is N-[5-(4-Acetyl-3-hydroxy-2-propylphenoxy)pentyl]-N'-[4-(3-pyridinyl)butyl]urea.

43. A method, in accordance with claim 30, wherein the compound of formula I is 3-(4-acetyl-3-hydroxy-2-propylphenoxy)methyl-N-[4-(3-pyridinyl)butyl]benzamide.

* * * * *